(12) United States Patent
Albed Alhnan

(10) Patent No.: US 12,171,881 B2
(45) Date of Patent: Dec. 24, 2024

(54) SOLID FORMS AND METHODS OF PREPARING THE SAME

(71) Applicant: University of Central Lancashire, Preston (GB)

(72) Inventor: Mohamed Albed Alhnan, Preston (GB)

(73) Assignee: University of Central Lancashire, Preston (GB)

( * ) Notice: Subject to any disclaimer, the term of this patent is extended or adjusted under 35 U.S.C. 154(b) by 0 days.

(21) Appl. No.: 18/120,054

(22) Filed: Mar. 10, 2023

(65) Prior Publication Data

US 2024/0041776 A1    Feb. 8, 2024

Related U.S. Application Data

(63) Continuation of application No. 17/178,598, filed on Feb. 18, 2021, now Pat. No. 11,622,940, which is a continuation of application No. 15/770,365, filed as application No. PCT/GB2016/053376 on Oct. 31, 2016, now Pat. No. 10,952,969.

(30) Foreign Application Priority Data

Oct. 29, 2015   (GB) ..................... 1519128

(51) Int. Cl.
| | | |
|---|---|---|
| A61K 9/20 | (2006.01) | |
| A23L 33/00 | (2016.01) | |
| A23L 33/10 | (2016.01) | |
| A23P 30/00 | (2016.01) | |
| A61K 31/522 | (2006.01) | |
| A61K 31/549 | (2006.01) | |
| B29C 64/106 | (2017.01) | |
| B29C 64/118 | (2017.01) | |
| B29K 33/04 | (2006.01) | |
| B29K 105/00 | (2006.01) | |
| B33Y 10/00 | (2015.01) | |
| B33Y 30/00 | (2015.01) | |
| B33Y 50/02 | (2015.01) | |
| B33Y 80/00 | (2015.01) | |

(52) U.S. Cl.
CPC ............ *A61K 9/2072* (2013.01); *A23L 33/00* (2016.08); *A23L 33/10* (2016.08); *A23P 30/00* (2016.08); *A61K 9/2027* (2013.01); *A61K 9/2095* (2013.01); *A61K 31/522* (2013.01); *A61K 31/549* (2013.01); *B33Y 10/00* (2014.12); *B33Y 30/00* (2014.12); *B33Y 50/02* (2014.12); *B33Y 80/00* (2014.12); *B29C 64/106* (2017.08); *B29C 64/118* (2017.08); *B29K 2033/04* (2013.01); *B29K 2039/06* (2013.01); *B29K 2105/0035* (2013.01)

(58) Field of Classification Search
None
See application file for complete search history.

(56) References Cited

U.S. PATENT DOCUMENTS

| | | | |
|---|---|---|---|
| 3,113,076 | A | 12/1963 | Jacobs |
| 6,365,183 | B1 | 4/2002 | Edgren et al. |
| 10,952,969 | B2 | 3/2021 | Albed Alhnan |
| 11,622,940 | B2 | 4/2023 | Albed Alhnan |
| 2006/0177496 | A1 | 8/2006 | McAllister et al. |
| 2007/0259010 | A1 | 11/2007 | Yoo et al. |
| 2008/0063709 | A1 | 3/2008 | Elliot et al. |
| 2018/0311169 | A1 | 11/2018 | Albed Alhnan |
| 2021/0369622 | A1 | 12/2021 | Alhnan |

FOREIGN PATENT DOCUMENTS

| | | |
|---|---|---|
| CN | 204428460 U | 7/2015 |
| WO | 2003092633 A2 | 11/2003 |
| WO | 2016038356 A1 | 3/2016 |
| WO | 2017072536 A1 | 5/2017 |

OTHER PUBLICATIONS

International Search Report and Written Opinion of PCT/GB2016/053376, dated Jan. 18, 2017, 10 Pages.
Search Report of GB1519128.1, dated Aug. 24, 2016, 4 Pages.
Goyanes et al., Fused-Filament 3D Printing (3DP) for Fabrication of Tablets, 2014, International Journal of Pharmaceutics, vol. 476(1-2), pp. 88-92.
Goyanes et al., 3D Printing of Modified-Release Aminosalicylate (4-ASA and 5-ASA) Tablets, 2015, European Journal of Pharmaceutical and Biopharmaceutics, vol. 89, pp. 157-162.
Skowyra et al., Fabrication of Extended-Release Patient-Tailored Prednisolone Tablets via Fused Deposition Modelling (FDM) 3D Printing, 2015, European Journal of Pharmaceutical Sciences, vol. 68, pp. 11-17.

*Primary Examiner* — Robert A Wax
*Assistant Examiner* — Quanglong N Truong
(74) *Attorney, Agent, or Firm* — Linda B. Huber; Nixon Peabody LLP

(57) ABSTRACT

The present invention relates to a solid form, particularly to a 3D-printed immediate release solid dosage form (e.g. based on a pharmaceutical, nutraceutical, or food supplement composition). To overcome some of the solubility and disintegration problems inherited by 3D-printed solid dosage forms, the solid form comprises one or more channels, generally in the form of tubular passages or grooves, through the body of the solid form or the surface thereof.

25 Claims, 13 Drawing Sheets

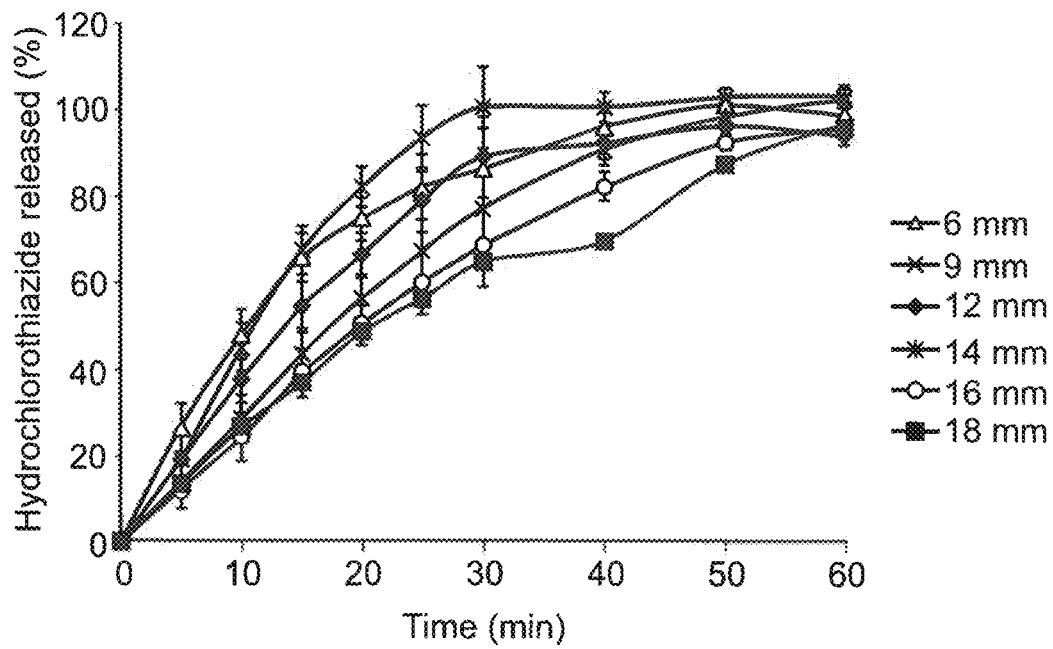
Fig. 1
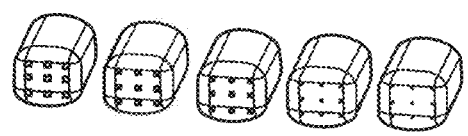
(a)
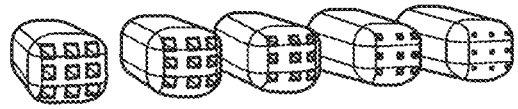
(b)
Fig. 2

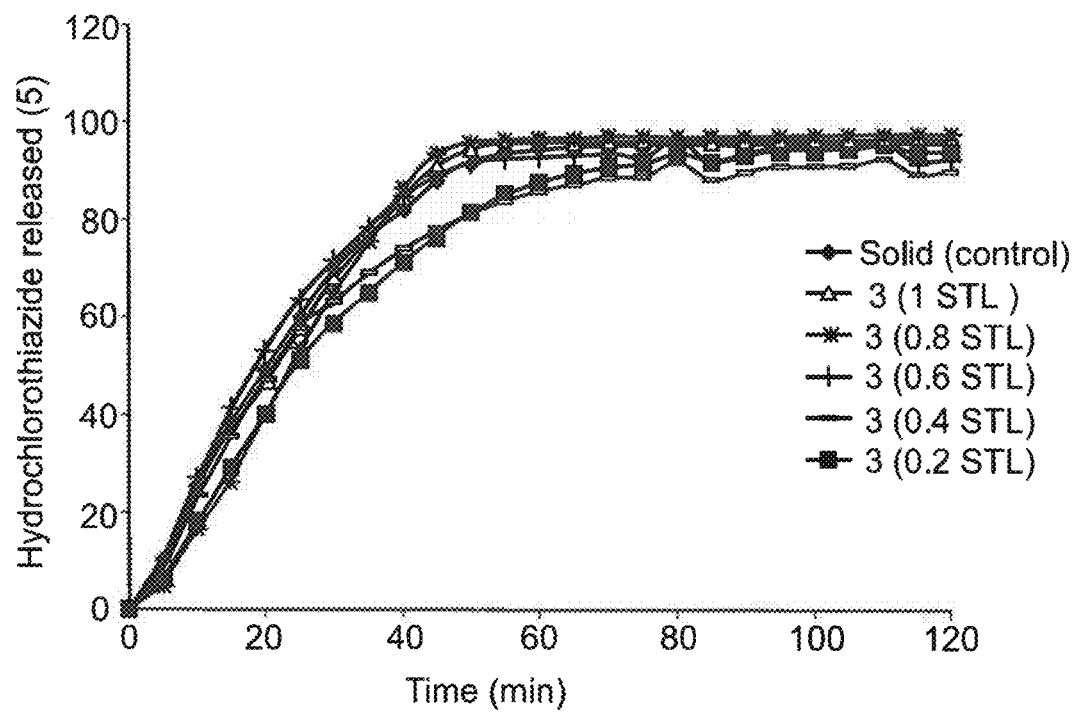
Fig. 7
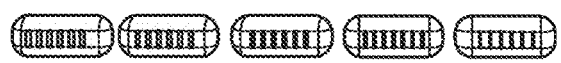
(a)
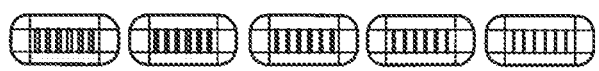
(b) Fig. 8

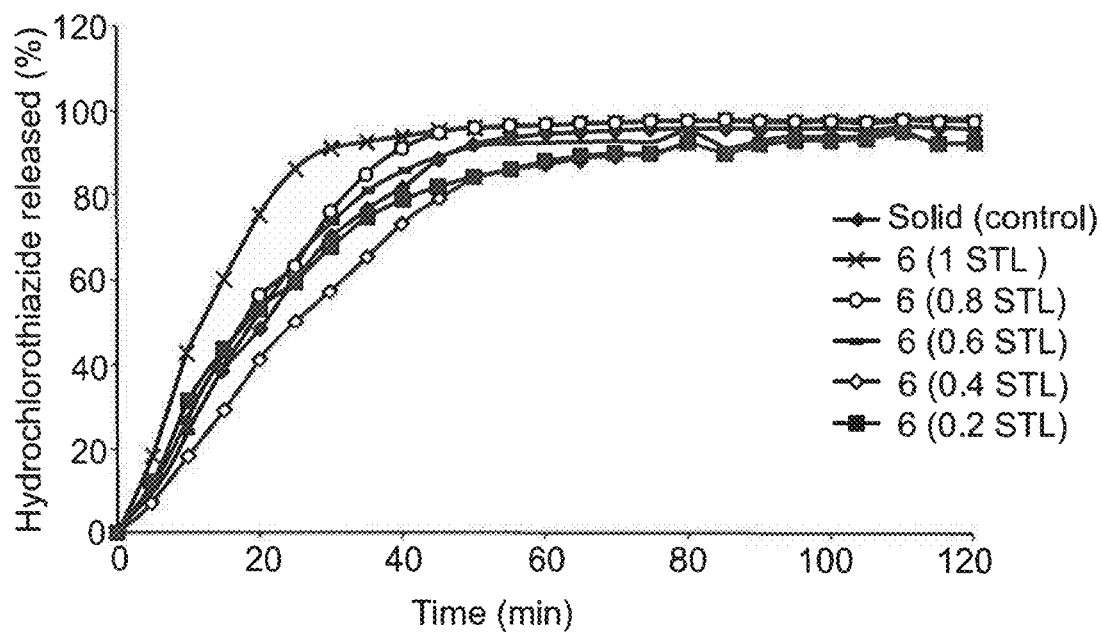
Fig. 9
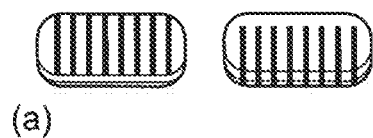
(a)
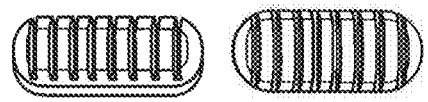
(b) Fig. 10

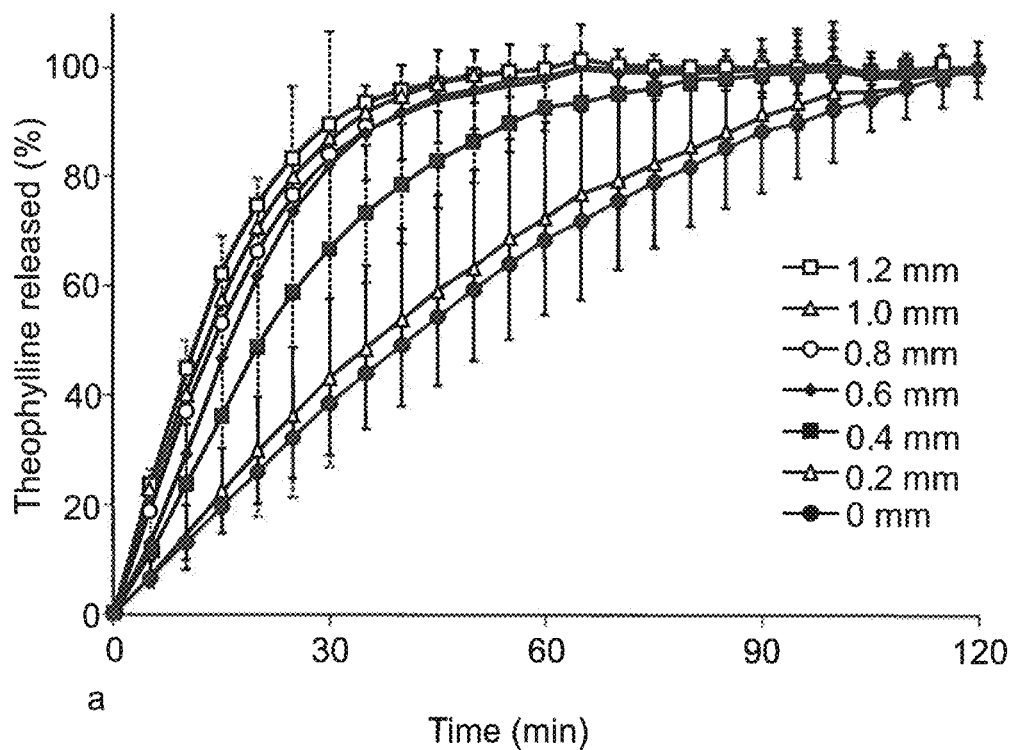
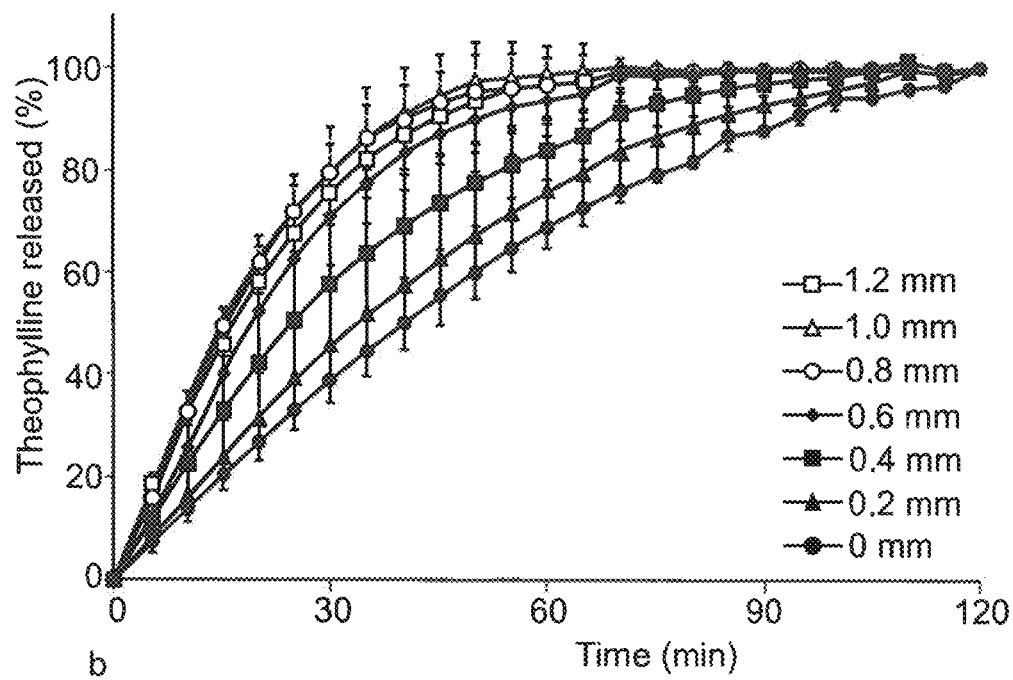
Fig. 18

SOLID FORMS AND METHODS OF PREPARING THE SAME

CROSS-REFERENCE TO RELATED APPLICATIONS

This application is a continuation of U.S. patent application Ser. No. 17/178,598 filed Feb. 18, 2021, which is a continuation of Ser. No. 15/770,365 filed Apr. 23, 2018, now U.S. Pat. No. 10,952,969, issued on Mar. 23, 2021, which is a National Phase of International Application No. PCT/GB2016/053376 filed Oct. 31, 2016, which designated the U.S. and that International Application was published under PCT Article 21(2) in English. This application also includes a claim of priority under 35 U.S.C. § 119(a) and § 365(b) to British patent application No. GB 1519128.1 filed Oct. 29, 2015, the entirety of which is hereby incorporated by reference.

INTRODUCTION

The present invention relates to a solid form, particularly to a solid dosage form (e.g. based on a pharmaceutical, nutraceutical, or food supplement composition), more particularly to 3D-printed immediate release solid dosage forms. The invention also relates to a solid dosage form; a solid dosage form for use in therapy; a method of preparing (or printing) a solid form or solid dosage form, including computer-implemented methods along with relevant software and hardware (e.g. a system configured or operable to implement said computer-implemented method), and a solid form obtainable from such methods.

BACKGROUND

The production and consumption of medicines, nutraceuticals, and food supplements (collectively referred to herein as "healthcare dosage forms"), in solid dosage form (e.g. tablets, implants, etc.) is ever increasing, not least due to an increased reliance on such products by national health services and the like in an increasingly health-conscious society. Where possible, solid dosage forms tend to be most preferred, relative to other formulations (e.g. injectable liquid formulations), due to their ease of administration (i.e. usually orally) which gives rise to better patient compliance, storability and transportability (low space requirements and ease of packaging), high stability (longer lifetimes—less degradation). However, despite the significant advantages of solid dosage forms over other dosage forms, they are often more onerous to manufacture (in terms of the number of both ingredients and processing steps) and are generally only cost effective to produce on large scale, meaning large manufacturing facilities with sophisticated equipment is usually required. These manufacturing limitations have a detrimental impact on consumer choice and/or the customisability of healthcare dosage forms since, for example, it is impractical and non-cost effective to mass produce a wide variety of different dosages for a given medicament via conventional manufacturing techniques. Consumers (e.g. patients) and healthcare professionals (e.g. doctors, pharmacists) must therefore make the best of the limited variety of dosages available, as dictated by the suppliers rather than a consumer's need.

Since the advent of 3-dimensional (3D) printing in the early 1980s, a number of researchers have attempted to make viable use of 3D printing technology to fabricate healthcare solid dosage forms. For instance, for well over a decade, MIT and Therics, Inc. have collaborated in the development of viable pill printing machines which utilise 3D printers to print solid pharmaceutical dosage forms in situ. The technology forms pills via a multi-layered 3D printing process involving precise printing of doses of a liquid drug solution onto thin layers of fine powder before further layers are then applied (e.g. further powder, binder, etc.). Examples of such processes are disclosed in earlier publications, such as WO95/11007 (MASSACHUSETTS INSTITUTE OF TECHNOLOGY) and WO03/092633 (THERICS, INC.), which describe inter alia the production of solid dosage forms having various structures and drug release profiles. However, regulatory approval (e.g. by the FDA or MHRA) for such 3D drug printing systems still remains elusive, and for the time being they are suitable only for low dose drug products, partly owing to the limited solubility of many drugs within the relevant ink solutions. As such, patient choice would still be very limited, as would the options of a doctor or pharmacist in providing specially-tailored treatments. Furthermore, resolution and shape of the solid dosage form still remains an issue. However, a particular issue with prior art 3D printing systems such as these is that the large number of different ingredients (and thus different printing cartridges etc.) needed to produce viable dosage forms imparts a high degree of complexity, user-unfriendliness, which in turn increases the likelihood of manufacturing errors, machine breakdown and malfunction, quality control variation, and regulatory viability (i.e. the FDA is less likely to approve drug printing systems which are prone to too many variables that may impact on the quality of the drug product). A further issue is the poor stability of some drug substances in liquid ink formulations. This can severely limit the shelf-life of the drug source, thus posing large regulatory and cost issues.

The present applicant has developed 3D-printing technologies, more specifically fused filament fabrication (FFF) technologies, to address one or more of the aforementioned problems inherent in the prior art, as illustrated in co-pending application PCT/GB2015/052595 (filed 8 Sep. 2015), which is hereby incorporated by reference. In addressing such problems, the applicant deploys 3D-printable filaments in the 3D-printing of solid dosage forms. Such filaments generally contain carrier materials which, for instance, serve as a vehicle for carrying active ingredients during both the printing process itself and within the solid dosage forms produced thereby. Such carrier materials are generally polymers with characteristics (e.g. molecular weight) complementary for filaments and their formation methods, the 3D printing process, and the desired solid dosage form. However, the applicants have found that in some cases, characteristics that are advantageous in terms of the filament and printing process can be sub-optimal for disintegration and/or dissolution of the final solid dosage form. For certain dosage forms, such as immediate release formulations, disintegration and/or dissolution profiles are important for inter alia regulatory compliance.

It is therefore an object of the present invention to solve at least one or more of the aforementioned problems. It is a particular object of the invention to provide a solution to the problem of sub-optimal disintegration and/or dissolution of 3D-printed solid forms.

SUMMARY OF THE INVENTION

According to an aspect of the present invention there is provided a solid form, suitably as defined herein. Such solid forms suitably comprise one or more channels therein (or therethrough—these terms are interchangeable), whether within the body of the solid form and/or the surface thereof.

According to a further aspect of the present invention there is provided a solid dosage form, suitably as defined herein.

According to a further aspect of the present invention there is provided a solid dosage form of a pharmaceutical, nutraceutical, or food supplement composition, suitably as defined herein.

According to a further aspect of the present invention there is provided a solid dosage form for use in therapy (or for use in the manufacture of a medicament), suitably as defined herein.

According to a further aspect of the present invention there is provided a method of preparing a solid form (e.g. a solid dosage form as defined herein), suitably as defined herein.

According to a further aspect of the present invention there is provided a computer-implemented method of preparing a solid form (e.g. a solid dosage form as defined herein), suitably as defined herein.

According to a further aspect of the present invention there is provided a solid form (e.g. a solid dosage form as defined herein) obtainable by, obtained by, or obtained directly by the method (or computer-implemented method) of preparing a solid form, suitably as defined herein.

According to a further aspect of the present invention there is provided a solid form printing apparatus, suitably as defined herein.

According to a further aspect of the present invention there is provided a computer for operating a solid form printing apparatus, suitably as defined herein.

According to a further aspect of the present invention, there is provided a computer program, comprising solid form printing software code for performing the computer-implemented method defined herein when the computer program is run on a computer.

According to a further aspect of the present invention, there is provided a computer-readable medium comprising solid form printing software code executable to cause a computer to perform the computer-implemented method defined herein when the software code is executed on a computer.

According to a further aspect of the present invention, there is provided a use of a solid form, suitably as defined herein.

Any features, including optional, suitable, and preferred features, described in relation to any particular aspect of the invention may also be features, including optional, suitable and preferred features, of any other aspect of the present invention.

BRIEF DESCRIPTION OF THE DRAWINGS

For a better understanding of the invention, and to show how embodiments of the same are put into effect, reference is now made, by way of example, to the following diagrammatic drawings, in which:

FIG. 1 shows % drug (hydrochlorothiazide) release profiles over time based on in vitro dissolution tests for standard-formulated unchannelled 3D-printed Eudragit E PO-based tablets of varying length dimensions (L=6, 9, 12, 14, 16, 18 mm).

FIG. 2 shows (a) photographs; and (b) rendered images; of tablets (with the same overall volume X=17.185, Y=6.805, Z=6.249) with 9 built-in long channels with increasing square channels (0.2, 0.4, 0.6, 0.8 and 1.0 mm).

FIG. 7 shows % drug (hydrochlorothiazide) release profiles over time based on in vitro dissolution tests for the channelled 3D-printed Eudragit E PO-based tablets of FIG. 6 as compared to a solid control.

FIG. 8 shows (a) photographs; and (b) rendered images; of tablets (with substantially the same overall volume X=17.185, Y=6.805, Z=6.249) with 6 built-in short channels with increasing sized rectangle channels (0.2, 0.4, 0.6, 0.8 and 1.0 mm).

FIG. 9 shows % drug (hydrochlorothiazide) release profiles over time based on in vitro dissolution tests for the channelled 3D-printed Eudragit E PO-based tablets of FIG. 8 as compared to a solid control.

FIG. 10 shows (a) photographs; and (b) rendered images; of tablets (with substantially the same overall volume X=18, Y=7.13, Z=6.548) with 8 built-in deep-groove-shaped channels 0.6 mm in size (i.e. shortest dimension=width of the channel/groove).

FIG. 18, panels a and b, show theophylline release profiles for a) 1.0 mm blocks and b) 1.5 mm blocks over with varying interblock spacings.

DETAILED DESCRIPTION OF THE INVENTION

Definitions

Figure 3:
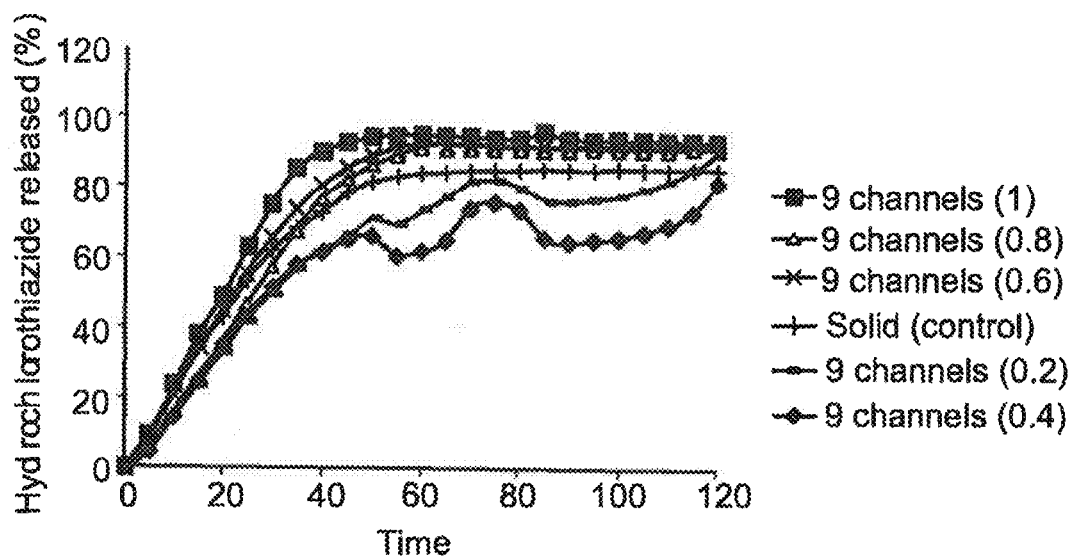
FIG. 3 shows % drug (hydrochlorothiazide) release profiles over time based on in vitro dissolution tests for the channelled 3D-printed Eudragit E PO-based tablets of FIG. 2 as compared to a solid control.

Unless otherwise stated, the following terms used in the specification and claims have the following meanings set out below.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

For the avoidance of doubt, it is hereby stated that the information disclosed earlier in this specification under the heading "Background" is relevant to the invention and is to be read as part of the disclosure of the invention.

Unless stated otherwise, any reference herein to the term "melt" (or its derivatives), especially in the context of melting filaments, suitably includes a glass transition or softening of a given material, suitably to allow extrusions thereof (e.g. through a nozzle). However, the term "melt" in the context of a defined "melting point" of a substance is as defined as per the art—a phase transition from solid to liquid.

Herein, references to "glass transition temperature" or "$T_g$" suitably refers to the temperature at which a material softens (e.g. to allow extrusion thereof). Suitably, glass transition temperatures (Tg) of materials described herein may be determined by a standard test method, suitably using dynamic mechanical analysis—a suitable test includes the testing protocol defined by ASTM E1640. Differential Scanning calorimetry (DSC) may also be utilised. For instance, glass transition temperatures may be discerned using the protocols set forth in ASTM E1356 and ASTM D7426. It will be understood by those skilled in the art that references herein to a particular material's glass transition temperature falling within a certain temperature range is intended to mean that at least one glass transition temperature of said material (which may or may not have multiple glass transition temperatures) falls within said temperature range. Suitably unqualified references to a "glass transition temperature" means at least one, suitably means the lowest glass transition temperature, and may suitably mean the glass transition temperature which absorbs the most thermal energy (or is most endothermic). The key, which is self-evident to those skilled in the art, is that sufficient softening of said material occurs under a particular set of circumstances (e.g. at the printing nozzle, where a filament needs to be softened in order to be extruded during the printing process, after which resolidification or rehardening may take place).

Unless stated otherwise, the term "viscosity" as used herein refers to a viscosity determined by means of a Brookfield viscometer (UL adapter/30 rpm/20° C.) in accordance with testing protocols defined by Ph. Eur. 2.2.10 or USP<912>method II.

Unless stated otherwise, any reference herein to an "average" value is intended to relate to the mean value.

Where a composition is said to comprise a plurality of stipulated ingredients (optionally in stipulated amounts of concentrations), said composition may optionally include additional ingredients other than those stipulated. However, in certain embodiments, a composition said to comprise a plurality of stipulated ingredients may in fact consist essentially of or consist of all the stipulated ingredients.

Herein, where a composition is said to "consists essentially of" a particular component, said composition suitably comprises at least 70 wt % of said component, suitably at least 90 wt % thereof, suitably at least 95 wt % thereof, most suitably at least 99 wt % thereof. Suitably, a composition said to "consist essentially of" a particular component consists of said component save for one or more trace impurities.

Where the quantity or concentration of a particular component of a given composition is specified as a weight percentage (wt % or % w/w), said weight percentage refers to the percentage of said component by weight relative to the total weight of the composition as a whole. It will be understood by those skilled in the art that the sum of weight percentages of all components of a composition will total 100 wt %. However, where not all components are listed (e.g. where compositions are said to "comprise" one or more particular components), the weight percentage balance may optionally be made up to 100 wt % by unspecified ingredients (e.g. a diluent, such as water, or other non-essentially but suitable additives).

Herein, unless stated otherwise, the term "parts" (e.g. parts by weight, pbw) when used in relation to multiple ingredients/components, refers to relative ratios between said multiple ingredients/components. Expressing molar or weight ratios of two, three or more components gives rise to the same effect (e.g. a molar ratio of x, y, and z is $x_1:y_1:z_1$ respectively, or a range $x_1-x_2:y_1-y_2:z_1-z_2$). Though in many embodiments the amounts of individual components within a composition may be given as a "wt %" value, in alternative embodiments any or all such wt % values may be converted to parts by weight (or relative ratios) to define a multi-component composition. This is so because the relative ratios between components is often more important than the absolute concentrations thereof in the liquid pharmaceutical compositions of the invention. Where a composition comprising multiple ingredients is described in terms of parts by weight alone (i.e. to indicate only relative ratios of ingredients), it is not necessary to stipulate the absolute amounts or concentrations of said ingredients (whether in toto or individually) because the advantages of the invention can stem from the relative ratios of the respective ingredients rather than their absolute quantities or concentrations. However, in certain embodiments, such compositions consists essentially of or consist of the stipulated ingredients and a diluents (e.g. water).

The term "mole percent" (i.e. mol %) is well understood by those skilled in the art, and the mol % of a particular constituent means the amount of the particular constituent (expressed in moles) divided by the total amount of all constituents (including the particular constituent) converted into a percentage (i.e. by multiplying by 100). The concept of mol % is directly related to mole fraction.

The term "substantially free", when used in relation to a given component of a composition (e.g. "a liquid pharmaceutical composition substantially free of compound X"), refers to a composition to which essentially none of said component has been added. When a composition is "substantially free" of a given component, said composition suitably comprises no more than 0.001 wt % of said component, suitably no more than 0.0001 wt % of said component, suitably no more than 0.00001 wt %, suitably no more than 0.000001 wt %, suitably no more than 0.0000001 wt % thereof, most suitably no more than 0.0001 parts per billion (by weight).

The term "entirely free", when used in relation to a given component of a composition (e.g. "a liquid pharmaceutical composition entirely free of compound X"), refers to a composition containing none of said component.

Suitably, unless stated otherwise, where reference is made to a parameter (e.g. pH, pKa, etc.) or state of a material (e.g. liquid, gas, etc.) which may depend on pressure and/or temperature, suitably in the absence of further clarification such a reference refers to said parameter at standard ambient temperature and pressure (SATP). SATP is a temperature of 298.15 K (25° C., 77° F.) and an absolute pressure of 100 kPa (14.504 psi, 0.987 atm).

Herein, the term "particle size" or "pore size" refers respectively to the length of the longest dimension of a given particle or pore. Particle and pore sizes may be measured using methods well known in the art, including a laser particle size analyser and/or electron microscopes (e.g. transmission electron microscope, TEM, or scanning electron microscope, SEM).

Herein, unless stated otherwise, the scope of the term "parallel" or "substantially parallel" will be readily understood by those skilled in the relevant art. Suitably the term "parallel" is a qualitative rather than a quantitative feature, especially given that any quantitative measure would be dependent on the scale and accuracy of any relevant measurements. However, two or more entities may be considered parallel where said entities are +/−10° from a perfectly parallel arrangement, more suitably +/−5° from a perfectly parallel arrangement, more suitably +/−1° from a perfectly parallel arrangement.

Herein, unless state otherwise, references to "channels" within a solid form suitably refer to continuous or extended regions within the body of the solid form characterised by either void space or a material which is otherwise dissimilar (suitably by composition and/or properties, especially solubility properties) to surrounding material with the solid form. As such, a solid form may comprise channels characterised by tubular passages, trenches, or grooves of either void space or distinct material(s). Such channels may be open- or close-ended and/or open- or close-sided, though suitably at least part of such channels are linked to (or otherwise flow into) the exterior of the solid form. Channels are well-defined paths within a body. A body characterised by a percentage of void space dispersed homogenously therein (e.g. merely a lower density form of the body) does not constitute a body with channels. Moreover, a void core within a hollow tablet (with an outer shell) does not constitute a channel either. However, if that same body had its % void space localised into one or more discrete channels through/within the body (i.e. such that void spaces were linked to form one or more continuous channels), this could constitute a body with channels. Suitably a channel may be defined as having a minimum width or diameter.

Herein, unless stated otherwise, references to a shortest or a longest dimension of any particular entity (e.g. solid form, cross-section of a channel) will be well understood by the skilled person depending on the context. Though "dimensions" (e.g. x, y, z or length, width, depth) of any particular shape or entity may be arbitrarily assigned relative to said shape or entity, generally the skilled person would assign dimensions based on symmetry, for instance, assigning an origin (e.g. x=0, y=0, z=0) at a centre of maximum symmetry (e.g. at a centre of a square, rectangle, circle, ellipse, cube, cuboid, sphere, ellipsoid, etc.). Such conventions better enable the designation of a shortest dimension, which may then be considered as the dimension holding the shortest path between one side (or face) and another of any given shape or entity. The longest dimension may be the converse.

Herein, unless stated otherwise, references to "immediate release" have the ordinary meaning understood by those skilled in the pharmaceutical arts. Suitably "immediate release" may be defined in line with United States Pharmacopeia (USP) and Food and Drug Administration (FDA) standards and tested accordingly in line with standard dissolution tests (e.g. Chapter 711 USP). Suitably, immediate-release means that at least 75% of the active pharmaceutical ingredient (API) is dissolved within 45 minutes, but also encompasses rapid-release (≥85% API dissolved within 30 minutes) and very rapid release (≥85% API dissolved within 15 minutes). The skilled person can refer to European Pharmacopoeia 8.0. Strasbourg, France: Council of Europe; European Directorate for the Quality of Medicine; 2014 for further details.

General Points and Advantages Relating to the Invention

The present invention generally relates to solid forms, especially 3D-printed solid forms (e.g. printed using 3D-printing technologies such fused filament fabrication (FFF) methods), such as pharmaceutical, nutraceutical, or food supplement solid dosage forms. Such solid forms suitably comprise one or more channels therein. Such channels suitably facilitate overall disintegration and/or dissolution of the solid form within an appropriate medium—in the case of immediate release pharmaceutical solid dosage forms the relevant medium is suitably fluids of the GI tract, preferably the upper GI tract.

Such channels are particular useful for facilitating dissolution of 3D-printed solid dosage forms which, by virtue of the parameters of the printing process, will generally comprise carrier materials and/or excipients which can otherwise inhibit disintegration and/or dissolution. For instance, FFF 3D printing generally involves printing with filaments comprising carrier materials that imbue the filaments with glass transition temperatures ($T_g$) appropriate for 3D printing (i.e. the filaments must be sufficiently stiff and robust for their conveyance within a 3D printer, but also capable of sufficient softening within printing nozzles during printing). Such a balance of stiffness and flexibility is generally achieved by deploying carrier materials (e.g. polymers) having a sufficiently high molecular weight, which can in turn yield solid dosage forms with disintegration and solubility properties unsuitable for immediate release applications. The present invention involves the recognition of the problem, especially in the context of 3D-printed solid forms, and the solution which involves the judicious use of channels to improve the disintegration and solubility characteristics of such solid forms, especially where rapid solubility is required.

Such problems generally do not arise for solid forms prepared by conventional manufacturing techniques (e.g. tablets form via standard granulation and compression methods), where the disintegration and solubility-inhibiting carrier materials required for effective 3D printing are not employed.

As such, the present invention represents a further contribution by the applicants to the art of 3D-printed solid forms, especially 3D-printed immediate release pharmaceutical solid dosage forms.

Solid Form

The present invention provides a solid form. The solid form suitably comprises one or more channels. The channel (s) suitably extend within/through the body (i.e. bulk) and/or surface of the solid form. The channel(s) may comprise or consist essentially of empty space, and may thus resemble hollow tube(s) (e.g. within and through the body of the solid form) and/or grooves or indentations within one or more surface(s) of the solid form. Such channels suitably facilitate disintegration and/or dissolution of the solid form within a target medium. As such, instead of or in addition to empty space the channels may suitably comprise or consist essentially of a material(s) which disintegrates and/or dissolves in the target medium (suitably at a faster rate than other parts or the bulk of the solid form), suitably so as to yield channels comprising empty space during the disintegration and/or dissolution process within the target medium.

The solid form is suitably a printed solid form, most suitably a 3D-printed solid form (i.e. a solid 3-dimensional object printed using 3D-printing technology). The 3D-printed solid form is suitably a solid form printed via fused filament fabrication (FFF) printing. As such, the 3D-printed solid form suitably comprises a filament composition as defined herein. Suitably said filament composition or filament has a glass transition temperature as defined herein. Suitably, the solid form has a glass transition temperature as defined herein (which may be suitably the same $T_g$ as that of any corresponding printing/filament composition).

It is in the context of printed solid forms that disintegration and/or dissolution properties can pose the greatest challenges.

In principle, the solid form may be any solid object, though suitably the solid form is designed to disintegrate and/or dissolve, suitably in a fluid (preferably liquid) medium, suitably in an aqueous medium, suitably within bodily fluids (e.g. within the gastrointestinal tract).

The solid form suitably has at least one plane of symmetry, suitably at least two.

In an embodiment, the solid form is a pharmaceutical, nutraceutical, or food supplement solid dosage form. In a particular embodiment, the solid form is a pharmaceutical solid dosage form, for example, a tablet. Most suitably, the solid form is an immediate release solid dosage form. The immediate release solid dosage form suitably releases at least 75% of active ingredient(s) within a 45 minute period, suitably releases at least 85% of active ingredient(s) within a 30 minute period, and may suitably release at least 85% of the active ingredient(s) within a 15 minute period. The skilled person may refer to European Pharmacopoeia 8.0. Strasbourg, France: Council of Europe; European Directorate for the Quality of Medicine; 2014 for further details. Suitably the immediate release solid dosage form disintegrates and/or dissolves more quickly than a comparative solid dosage form, where the comparative solid dosage form has an identical mass and bulk composition to the immediate release solid dosage form but is free of channels (i.e. the comparative solid dosage form is fully solid). Suitably, the comparative solid dosage form would not qualify as an immediate release solid dosage form.

The solid dosage forms of the invention are generally discernible by chemical and/or microscopic analysis, which will suitably reveal whether or not the solid dosage form has been 3D-printed, for instance by extruded filaments in a layer-by-layer fashion.

The solid dosage form(s) of the invention are suitably for oral administration. Examples of solid dosage forms are tablets, capsules, granules, powders, beads and microcapsules. Most suitably the solid dosage form is a tablet or implant, most suitably a pharmaceutical tablet or medical implant (e.g. an implant which allows for sustained and/or controlled release of an active ingredient).

The solid dosage forms of the invention are advantageously customisable in terms of the type/nature of active ingredient dose, the dose of the active ingredient within the solid dosage form (be it an absolute dose per solid dosage form or the concentration of the active within the dosage form), the mass/volume of the solid dosage form (which is typically adaptable to vary the absolute dose of the active without changing the concentration of the active within the dosage form), the active release profile (which may be varied through judicious use and/or distribution of appropriate excipients, e.g. core-shell arrangements for delayed or sustained release), or shape and appearance (including novelty shapes, colours, and patterns, such as those that may help encourage medication compliance for particular patients).

The longest dimension ($D_{max}$)) of the solid dosage form (e.g. the longest of the X, Y, Z parameters shown in the Examples) is suitably greater than or equal to 3 mm, suitably greater than or equal to 5 mm, suitably greater than or equal to 8 mm, suitably greater than or equal to 10 mm, suitably greater than or equal to 12 mm. The longest dimension of the solid dosage form is suitably less than or equal to 30 mm, suitably less than or equal to 25 mm, suitably less than or equal to 20 mm, suitably less than or equal to 15 mm.

The shortest dimension ($D_{min}$) of the solid dosage form (i.e. not necessarily the thinnest part but the maximum length of the thinnest dimension, or the shortest of the X, Y, Z parameters shown in the Examples) is suitably greater than or equal to 3 mm, suitably greater than or equal to 5 mm, suitably greater than or equal to 8 mm, suitably greater than or equal to 10 mm, suitably greater than or equal to 12 mm. The shortest dimension of the solid dosage form is suitably less than or equal to 30 mm, suitably less than or equal to 25 mm, suitably less than or equal to 20 mm, suitably less than or equal to 15 mm.

Suitably, the overall channel-inclusive volume ($V_{tot}$) of the solid form (inclusive of the volume of any channels) is greater than or equal to 50 mm$^3$, suitably greater than or equal to 100 mm$^3$, suitably greater than or equal to 300 mm$^3$, suitably greater than or equal to 500 mm$^3$. Suitably, the overall channel-inclusive volume of the solid form is less than or equal to 5000 mm$^3$, suitably less than or equal to 3000 mm$^3$, suitably less than or equal to 1000 mm$^3$. For the purposes of assessing overall channel-inclusive volumes ($V_{tot}$), any channel openings at the surface of the solid form may be hypothetically closed by a "surface of best fit" formed by extrapolating the profile of the solid form across any such channel openings. The skilled person is capable of determining the "surface of best fit" to cover the channel openings, whether the hypothetical surface is to be curved or substantially flat. This may also be determined computationally by smoothing and normalisation functions, or by reference to the original "blueprint" (e.g. a CAD design) for the shape of the solid form without channels.

Suitably, the solid volume ($V_{sol}$) of the solid form (i.e. exclusive of the volume of any channels) is greater than or equal to 50 mm$^3$, suitably greater than or equal to 100 mm$^3$, suitably greater than or equal to 300 mm$^3$, suitably greater than or equal to 400 mm$^3$. Suitably, the solid volume ($V_{sol}$) of the solid form is less than or equal to 3000 mm$^3$, suitably less than or equal to 2000 mm$^3$, suitably less than or equal to 800 mm$^3$. The solid volume ($V_{sol}$) may be determined by techniques well known in the art, and may for instance be calculated by subtracting the volume of the channels from overall channel-inclusive volume ($V_{tot}$). This may also be determined computationally by reference to the original "blueprint" (e.g. a CAD design) for the shape of the solid form without channels and the final design with channels.

Suitably, the overall surface area ($A_{tot}$) of the solid form (including internal and external surfaces of the solid form, which thereby includes channels, and thereby includes any additional surface area introduced by the channels and thus excludes any previous external surface area lost by the introduction of channels), where said surface area is based on either exposed surface area or exposable surface area (e.g. where instead of being void space the channels are in fact voidable materials—e.g. dissolvable materials), is greater than or equal to 100 mm$^2$, suitably greater than or equal to 200 mm$^2$, suitably greater than or equal to 400 mm$^2$, suitably greater than or equal to 600 mm$^2$, suitably greater than or equal to 800 mm$^2$. Suitably, the overall surface area ($A_{tot}$) of the solid form is less than or equal to 5000 mm$^2$, suitably less than or equal to 3000 mm$^2$, suitably less than or equal to 2000 mm$^3$, suitably less than or equal to 1000 mm$^3$.

A "solid-volume-based surface area density" ($d_{Asol}$), based on the solid volume ($V_{sol}$) of the solid form (i.e. exclusive of the volume of any channels) may be expressed as:

$$d_{Asol} = \frac{A_{tot}}{V_{sol}}$$

where $A_{tot}$ is the overall surface area, and $V_{sol}$ is solid volume only, as described above.

Suitably the "solid-volume-based surface area density" ($d_{Asol}$) is greater than or equal to 0.8 mm$^{-1}$, suitably greater than or equal to 1.0 mm$^{-1}$, suitably greater than or equal to 1.2 mm$^{-1}$, suitably greater than or equal to 1.5 mm$^{-1}$, suitably greater than or equal to 1.7 mm$^{-1}$. Suitably the "solid-volume-based surface area density" ($d_{Asol}$) is less than or equal to 3.0 mm$^{-1}$, suitably less than or equal to 2.5 mm$^{-1}$, suitably less than or equal to 2.0 mm$^{-1}$, suitably less than or equal to 1.9 mm$^{-1}$.

Suitably, the channels ($V_{chan}$) constitute at least 2% of the overall channel-inclusive volume ($V_{tot}$) of the solid form, suitably at least 5%, suitably at least 10%, suitably at least 15%, suitably at least 20%, suitably at least 25%. As such, the percentage channel volume may be expressed as:

$$\frac{V_{chan}}{V_{tot}} \times 100$$

Suitably, the channels constitute at most 40% of the overall channel-inclusive volume of the solid form, suitably at most 30%, suitably at most 25%, suitably at most 20%.

Suitably, the solid form has a mass of greater than or equal to 50 mg, suitably greater than or equal to 80 mg, suitably greater than or equal to 250 mg, suitably greater than or equal to 500 mg, suitably greater than or equal to 1.0 g, suitably greater than or equal to 1.5 g. Suitably, the solid form has a mass of less than or equal to 5.0 g, suitably less than or equal to 3.0 g, suitably less than or equal to 2.0 g, suitably less than or equal to 1.5 g.

Channels of the Solid Form

The solid form suitably comprises one or more channels, more suitably a plurality of channels extending within the body (i.e. bulk) and/or surface(s) of the solid form. Suitably the solid form comprises three or more channels, suitably five or more, suitably 8 or more. Each individual channel is suitably characterised as a continuous extended region, and may be in the form of a tubular passage, corridor, vein, trench, or groove comprising or consisting essentially of void space or a "channel material" which differs from otherwise (non-channel) surrounding material. The solid form suitably comprises one type of channel, be it channel(s) comprising void space or channel(s) comprising channel material. However, in some embodiments, the solid form may comprise a mixture of channel types. For instance, some of the channel(s) may comprise void space, whilst other channel(s) may comprise channel material, suitably channel material that readily disintegrates. The use of channel material may help to impart a more robust structure to the solid form, whilst also providing "weak points" to facilitate disintegration and/or dissolution. Alternatively, however, such "weak points" may comprise the same material or composition as the body (or bulk) of the solid form, but sufficiently structurally weak (e.g. thin) to allow for rapid disintegration and/or dissolution of the dosage form. In some embodiments, one or more (suitably two or more) channels may be bridged, suitably be "weak points", whether the weak points are frangible (or disintegratable) portions of the body of the solid form (i.e. made of the same material as the body of the solid form) or channels of (suitably disintegratable and/or soluble) channel material.

Channel(s) extending through the body of the solid form are suitably tubular passages or veins, whereas channel(s) extending within surface(s) of the solid form are suitably trenches or grooves (though they may also be considered "veins", especially where the channel(s) are characterised by a channel material rather than void space). Such grooves may, in some embodiments, be optionally bridged deep grooves, for instance providing a radiator-like structure.

Suitably the or each channel is characterised by a particular cross-section ("channel cross-section"). Suitably the or each channel cross-section extends, and is substantially preserved (suitably in terms of shape and/or dimensions) along at least part of (suitably the majority of, and suitably the entire) length of the relevant channel, notwithstanding any cross-links or cross-bridges that may be optionally present along its length. Suitably the cross-section of such bridges are smaller than the relevant channel cross-section (so as not to block or close said channel) or such bridges are either frangible, distintegratable, or soluble (e.g. weak points of either channel material or frangible portions of the solid form body material). The cross-section of channels extending through the body of the solid form are suitably discernible by the relevant tubular cross-section, whilst the cross-section of surface channels may be extrapolated by imbuing any open surfaces/sides with a hypothetical "surface of best fit" (as described above in relation to calculations regarding the overall channel-inclusive volumes). Suitably the shape of the channel cross-section(s) are substantially uniform along their length. Suitably the dimensions (e.g. depth, perimeter, diameter) of the channel cross-section(s) are substantially uniform along their length. Suitably, non-uniformities in channel cross-section(s) are smooth or continuous variations (as per a continuous mathematical function). Suitably, any discontinuities in a channel cross-section are considered boundaries between different channels, even if said distinct channels are interconnected at the point of discontinuity.

Suitably any cross-bridges within a channel cross-bridge the shortest dimension of said channel.

The channel cross-section(s) are suitably defined by a 2-dimensional shape (suitably defined along X and Y axes with the origin at the point of maximum symmetry or a central point within the shape, whichever is most applicable by convention).

Suitably the shortest dimension ($D_{min}$) of the channel cross-section(s) is greater than or equal to 0.2 mm, suitably greater than or equal to 0.4 mm, suitably greater than or equal to 0.5 mm, suitably greater than or equal to 0.6 mm, suitably greater than or equal to 0.7 mm, suitably greater than or equal to 0.75 mm. Suitably, the channel cross-section can enclose a circle having diameter greater than or equal to 0.2 mm, suitably greater than or equal to 0.4 mm, suitably greater than or equal to 0.5 mm, suitably greater than or equal to 0.6 mm, suitably greater than or equal to 0.7 mm, suitably greater than or equal to 0.75 mm.

Suitably the longest dimension ($D_{max}$) of the channel cross-section(s) is less than or equal to 5.0 mm, suitably less than or equal to 4.0 mm, suitably less than or equal to 2.0 mm, suitably less than or equal to 1.2 mm.

The channel cross-section(s) are suitably independently selected from the group consisting of a: circle, ellipse, and a regular or irregular polygon (e.g. a hexagon, pentagon square, rectangle, or triangle). Suitably any polygonal channel cross-section(s) are regular polygons or otherwise rectangular. The solid form may comprise a plurality of channels having two or more different channel cross-sections (whether the variation is in the shape and/or dimensions).

The channel(s) may be open- or close-ended. However, suitably any channels within the body of the solid form have at least one open end or at least one closed end which disintegrates and/or dissolves more rapidly (in a relevant medium, such as water or bodily fluids, such as gastrointestinal fluids) than the body of the solid form.

The channel(s) may be open-sided (i.e. as per channels within a surface of the solid form) or close-sided. Moreover, the channel(s) may suitably be characterised by (deep) grooves, trenches, or slices within the solid form, optionally cross-links or bridges between opposite sides thereof. The depth (as distinct from end-to-end length, or side-to-side width) of such (deep) grooves or slices may constitute greater than or equal to 20% of the total depth of the solid form in the particular direction of the groove or slice, suitably greater than or equal to 40% of the total depth of the solid form, suitably greater than or equal to 50% of the total depth of the solid form, suitably, suitably greater than or equal to 70% of the total depth of the solid form.

Suitably, the channel(s) are in fluid communication with the exterior of (or an external surface of) the solid form (e.g. where the channel(s) comprise void space) or else are characterised by a path leading to the exterior of (or an external surface of) the solid form (e.g. where the channel(s) comprise or consist essentially of a channel material). However, in some embodiments, some internal channels may be entirely closed, but are suitably characterised by a path to the exterior of the solid form via channel material or "weak points" (i.e. frangible parts) of the body of the solid form.

Suitably the solid form comprises a plurality of (substantially) parallel channels. Suitably the solid form comprises a plurality of (substantially) equally-spaced channels (suitably equal with +/−10% of the mean average spacing, suitably +/−5%, suitably +/−2%, suitably +/−1%). Suitably the channels are both equally-spaced and parallel.

Suitably, the channel(s) are substantially linear, straight, or flat.

Suitably, the solid form comprises channel(s) which extend through the entire body of the solid form (i.e. form one surface to another, suitably double open-ended with openings or visible veins of channel material at both ends). In some embodiments, such double open-ended structures may also have a single open side (e.g. as per radiator-like structures formed by deep grooves). Alternatively, the solid form suitably comprises channel(s) with single open-ends (i.e. which do not extend throughout the entirety of the body of the solid form).

Suitably, the (or at least some) of the one or more channel(s) extend across the shortest dimension of the solid form, whether said channel(s) extend across the entire length of said dimension or only part thereof. In other embodiments, the (or at least some) of the one or more channel(s) extend across the longest dimension of the solid form, whether said channel(s) extend across the entire length of said dimension or only part thereof.

In a particular embodiment, the solid form is a pharmaceutical, nutraceutical, or food supplement solid dosage form with a plurality of (suitably square or rectangular cross-sectioned) channels extending through the (suitably the longest dimension of the) entire body of the solid dosage form. Suitably the shortest dimension of the cross-section of said channel(s) is at least 0.4 mm, suitably at least 0.6 mm. Suitably the channels are tubular, suitably double-open-ended, and suitably close-sided.

In a particular embodiment, the solid form is a pharmaceutical, nutraceutical, or food supplement solid dosage form with a plurality of (suitably square or rectangular cross-sectioned) channels extending through the shortest dimension entire body of the solid dosage form. Suitably the shortest dimension of the cross-section of said channel(s) is at least 0.4 mm, suitably at least 0.6 mm. Suitably the channels are tubular, suitably double-open-ended, and suitably close-sided.

In a particular embodiment, the solid form is a pharmaceutical, nutraceutical, or food supplement solid dosage form with a plurality of (suitably rectangular cross-sectioned/grooved) channels extending through (suitably the shortest dimension of) the entire (or part of) body of the solid dosage form. Suitably the shortest dimension of the cross-section of said channel(s) is at least 0.4 mm, suitably at least 0.6 mm. Suitably the channels are grooves (or slices), suitably double-open-ended, suitably with one open side/face. Suitably the channels resemble a radiator-type structure.

Though the channel(s) most suitably comprise, more suitably consist essentially of, void space (notwithstanding any intervening bridges along the length of said channel(s)), the benefits of the invention may still be realised when using channel(s) of "channel material", where the channel material is readily disintegratable, or otherwise soluble (e.g. in a relevant medium). Where channel material is used, suitably such material disintegrates and/or dissolves to either leave transiently-existing channel(s) comprising of consisting essentially of void space or to facilitate disintegration of the solid form. The channel material may depend on the application in question, and suitably depends upon the relevant medium. For instance, a solid dosage form according to the invention intended for immediate release will suitably comprise channel(s) of channel material which disintegrates and/or dissolves in the upper GI tract. Therefore, the chosen channel materials may suitably disintegrate and/or dissolve at acid pHs, suitably a pH between pH 0 and pH 5.

Suitably, where the channel(s) comprise or essentially consist of void space, such channel(s) are suitably permeable to a relevant medium in which the solid form is intended to disintegrate and/or dissolve. As such, the shape and size of the channel(s) and their corresponding cross-section(s) may be judiciously chosen to facilitate the passage of such a medium therethrough. Hydrodynamic flow may thus be an important consideration, which may be balanced with surface area considerations. Suitably the channel(s) expose a larger surface area of the solid form than would be otherwise exposed without the presence of said channel(s).

Suitably the solid dosage form may comprise a plurality of interconnected dosage sub-units (e.g. sub-parts of a solid dosage form). Suitably each dosage sub-unit is connected to one or more adjacent sub-units, suitably one or two adjacent sub-units. Suitably the dosage sub-units are interconnected by cross-links or bridges, suitably frangible, disintegratable (easy to disintegrate), and/or soluble cross-links. As such, the cross-links or bridges may be considered "weak points", which suitably facilitate more rapid disintegration and/or dissolution of the overall solid dosage form. For example, when a solid dosage form comprising such interconnect sub-units contacts a disintegration/dissolution medium (e.g. gastric fluid) the weak points (or cross-links) may suitably break to release a plurality of separated dosage sub-units, which may then exhibit a faster disintegration/dissolution profile than they otherwise would if they had remained interconnected. Suitably, each interconnected pair of dosage sub-units is connected by one or more cross-links therebetween, suitably by one cross-link therebetween.

The dosage sub-units may have (substantially) the same or different compositions to each other, most suitably the same composition. Suitably each dosage sub-unit independently comprises a solid dosage form composition as defined herein.

Suitably the cross-links or bridges comprise or consist essentially of the same material as at least one (preferably both or all) of the dosage sub-units to which they are connected.

The sub-units may be any shape or size. Suitably the individual sub-units are individual blocks, sheets, discs, or such like. Suitably each individual sub-unit is of substantially uniform thickness throughout (e.g. +/−5%). Suitably some or all of the plurality of sub-units are of substantially the same thickness (e.g. +/−5%) as each other.

Cross-links may intersect (most suitably in a substantially perpendicular manner) their corresponding sub-unit(s) at any point upon the sub-unit(s). In some embodiments, cross-link(s) may intersect at (substantially) the centre (or at least away from any edges or sides) of the sub-unit(s) to which they are connected. Suitably, however, cross-link(s) may intersect at a base, edge, or side of a sub-unit(s). In some embodiments, a mixture of intersection arrangements may prevail throughout the solid dosage form. In a particular embodiment, the solid dosage form resembles a radiator-like structure e.g. a row of (substantially) parallel sheets mutually interconnected at a base-edge thereof. Alternatively, the solid dosage form may comprise a plurality of (substantially) parallel blocks, sheets, or discs interconnected in a (substantially) coaxial manner via a cross-linking rod extending through the centre of the solid dosage form (i.e. interconnecting the sub-units substantially centrally). The solid dosage form may resemble a skeletal structure, with a series of space sub-units interlinked via one or more bridging elements.

By definition, such embodiments of solid dosage form comprise the aforesaid pre-defined channels between adjacent sub-units. Such channels are suitably pre-defined gaps or regions of void space in between the sub-units. As such, the solid sub-units may be "caplets" and the spaces therebetween "gaplets". Suitably any spacings between the caplets may conform to dimensions disclosed herein in relation to channel dimensions.

Suitably such interconnected-sub-unit-based solid dosage forms can disintegrate and/or dissolve more quickly within relevant dissolution mediate. Suitably, the cross-links (or "weak points", which suitably break or dissolve more quickly/easily than the sub-units themselves) facilitate separation of individual sub-units (e.g. sheets) to enable fast release profiles of any relevant active ingredients.

In an embodiment, a solid dosage form the dosage form comprises a plurality of individual mini-dosage forms or mini-dosage blocks ("caplets") of a predefined shape (e.g. disc shaped) interlinked, with pre-defined spaces in between ("gaplets"), by a series of bridging elements. Such solid dosage forms are suitably capped at each end with end caps which may be mini-dosage forms as well. Such end caps may facilitate swallowing. Each individual bridging element is suitably a member of one or more longitudinal bridges extending through or across the solid dosage form, suitably either along one of two opposite sides of the dosage form and/or through the middle of the dosage form in a substantially coaxial fashion.

Suitably, in any of the aforementioned embodiments, adjacent sub-units are spaced by a gap of at least 0.4 mm. Suitably the smallest dimension of the sub-units (suitably excluding any end caps), which is usually the thickness thereof, is at least 0.4 mm, suitably at least 0.6 mm, suitably at most 2.0 mm, suitably at most 1.5 mm, suitably about 1.0 mm.

Most suitably, a solid form of the invention disintegrates and/or dissolves faster than a comparative solid form without channel(s).

Composition of Solid Form

The solid form suitably comprises a carrier material, for instance, a carrier polymer. Suitably the carrier material is a vehicle or carrier (e.g. pharmaceutical vehicle or carrier) for one or more other ingredients of the solid form, for instance, a carrier for an active ingredient such as a pharmaceutically active ingredient. As such, the solid form may also suitably comprise an active ingredient. In addition, the solid form may comprise a variety of other ingredients depending on the application. For instance, where the solid form may comprise one or more additional pharmaceutical excipients and/or carriers where the solid form is a pharmaceutical solid dosage form.

Carrier Material(s)

The carrier material is suitably a carrier material suitable for use in 3D-printing, and especially suitable as a printable (and suitably meltable/softenable) carrier ingredient within filaments for FFF 3D-printing. Suitably the characteristics of the carrier material that facilitate 3D-printing are a source of disintegration and/or solubility problems in the final solid form, which are duly addressed by the present invention.

The solid form, or at least a part of the solid form through which one or more channel(s) pass, suitably comprises greater than or equal to 10 wt % carrier material (suitably excluding any plasticizer(s)), suitably greater than or equal to 20 wt %, suitably greater than or equal to 30 wt %, suitably greater than 50 wt %, suitably greater than or equal to 79 wt %. Suitably, solid forms of the invention comprise less than or equal to 99 wt % carrier material (suitably excluding any plasticizer(s)), suitably less than or equal to 90 wt %, suitably less than or equal to 80 wt %, suitably less than or equal to 60 wt %. In a particular embodiment, the solid form comprises 40-60 wt % carrier material, suitably 45-55 wt %.

The carrier material(s) suitably has or comprises one or compounds having a molecular weight of at least 2,000 g/mol, more suitably at least 5,000, more suitably at least 10,000, more suitably at least 20,000, more suitably at least 35,000, more suitably at least 45,000, suitably at least 100,000. Molecular weights are suitably cited in g/mol. Suitably molecular weights are average molecular weights, especially where they may refer to polymers.

The carrier material(s) suitably is or comprises one or compounds that is sparingly soluble, slightly soluble, very slightly soluble, practically insoluble, or insoluble according to the standard USP definitions (and standard tests defined therefore in the USP) as per the table below:

| Descriptive Term | Parts of solvent Required for 1 Part of Solute |
| --- | --- |
| Very soluble | Less than 1 |
| Freely soluble | From 1 to 10 |
| Soluble | From 10 to 30 |
| Sparingly soluble | From 30 to 100 |
| Slightly soluble | From 100 to 1,000 |
| Very slightly soluble | From 1,000 to 10,000 |
| Practically insoluble, or Insoluble | Greater than or equal to 10,000 |

The carrier material(s) suitably is or comprises one or compounds that is very slightly soluble, practically insoluble, or insoluble according to the standard USP definitions as per the table above. Suitably, the carrier material(s) suitably is or comprises one or compounds that is practically insoluble, or insoluble according to the standard USP definitions as per the table above.

The carrier material itself suitably has a melting point between 140 and 250° C., more suitably between 150 and 200° C., most suitably between 155 and 175° C.

Suitably the carrier material has a specific heat of between 0.1 and 1 cal/g ° C., most suitably between 0.3 and 0.5.

The carrier material suitably has a density between 1.1 and 1.6 g/mL, most suitably between 1.2 and 1.4.

The carrier material(s), especially where an immediate release solid dosage form is desired, is suitably selected from a carrier (suitably a cationic polymer or neutral polymer or copolymer) having a viscosity of no more than 50 mPa·s, suitably no more than 30 mPa·s, suitably no more than 10 mPa·s, though suitably having a viscosity of at least 1 mPa·s—most suitably a viscosity between 2 and 8 mPa·s. The carrier material(s), especially where an immediate release solid dosage form is desired, is suitably selected from a carrier having a molecular weight of at least 2,000 g/mol, more suitably at least 5,000, more suitably at least 10,000, more suitably at least 20,000, more suitably at least 35,000, more suitably at least 45,000, though suitably less than 1,000,000 g/mol, more suitably less than 100,000 g/mol—most suitably a molecular weight between 35,000 and 65,000 g/mol. The carrier material(s), especially where an immediate release solid dosage form is desired, is suitably selected from a carrier having a glass transition temperature (Tg) of at most 100° C., suitably at most 80° C., suitably at most 50° C., though suitably at least −10° C., more suitably at least 30° C., more suitably at least 35° C.—most suitably a Tg between 30 and 60° C. In some embodiments, the carrier material(s) may not have a glass transition temperature as such, though observed softening may still occur. The carrier material(s), especially where an immediate release solid dosage form is desired, is suitably an (optionally alkyl-, suitably methyl- or ethyl-) acrylate, methacrylate and/or ethacrylate copolymer (suitably comprising amine-containing monomeric units) suitably having a viscosity between 2 and 8 mPa·, suitably having a molecular weight between 35,000 and 65,000 g/mol, and/or suitably having a Tg between 30 and 60° C. In a particular embodiment, the relevant copolymer is poly(butyl methacrylate-co-(2-demethylaminoeethyl) methacrylate-co-methyl methacrylate), suitably in a respective monomeric molar ratio of 1:2:1 (+/−5% for each molar value of the ratio). The carrier material is suitably Eudragit E or Eudragit E PO.

In some embodiments, especially where an active ingredient has limited solubility in a target solubilisation medium (e.g. in the body), carrier material(s) such as polyvinylpyrrolidone polymers or polyvinylpyrrolidone-derived polymers may be employed. Such polymers can facilitate dissolution of an active ingredient that may otherwise exhibit limited solubility. In a particular embodiment, PVP K29-32 (a povidone) may be used. When present, suitably a PVP or PVP-based carrier is present (e.g. in a filament, solid dosage form, or core) at a concentration of between 20 and 80 wt %, suitably at a concentration between 40 and 60 wt %, suitably 45-55 wt %. PVP and PVP-based carrier polymers may be used alongside one or more filler(s), and optionally with other ingredients such as plasticizer(s). Mixtures of different PVP or PVP-based carriers may also or alternatively be used (e.g. PVPs of different molecular weights).

In some embodiments, polyalkyleneglycol and polyalkyleneglycol-derived polymers may be employed as a carrier polymer, such as a carrier material. In a particular embodiment the polyalkyleneglycol or polyalkyleneglycol-derived carrier polymer is a polyethyleneglycol (PEG) or polyethyleneglycol-derived carrier polymer. Suitably, wherever a PEG or PEG-based carrier polymer is deployed, at least a portion of the PEG or PEG-based carrier polymer has a molecular weight of at least 100,000, though suitably at most 1,000,000. However, a mixture of different polyalkyleneglycol and polyalkyleneglycol-derived polymers (e.g. PEG or PEG-based carrier polymers) may be incorporated within filaments and/or corresponding dosage forms. For instance, a high molecular weight PEG may be used alongside a relatively low molecular weight PEG to achieve an optimal balance of properties. Higher molecular weight PEG and PEG-based polymers (e.g. $M_w \geq 80,000$) can serve as carrier molecules, whereas lower molecular weight PEG and PEG-based polymers (e.g. $M_w$ 200-20000) may serve as plasticizers and/or solubility enhancers. Increasing the proportions of lower molecular weight PEGs is likely to lower the $T_g$ of the resulting filament. Moreover, increasing the proportions of lower $M_w$ PEGs also favours accelerated drug release. Suitably any PEG or PEG-based carrier polymers are used alongside one or more filler(s), though such polymers may be used with or without non-melting components.

The carrier material is suitably a polymer or mixture of polymers selected from the group consisting of an (optionally alkyl-) acrylate, methacrylate or ethacrylate polymer or copolymer, optionally comprising amine-containing monomeric units, a polyvinylpyrrolidone or polyvinylpyrrolidone-derived polymer or co-polymer, and a polyalkyleneglycol or polyalkyleneglycol-derived polymer or copolymer.

Since the solid form is suitably a 3D-printed solid form (for instance printed using a filament or appropriate ink source), suitably the solid form comprises one or more printable composition(s) (depending how many different filament or ink compositions are used in the printing of the solid form), for instance, a filament composition. Suitably the solid form essentially consists of or suitably consists of the one or more printable composition(s). In certain embodiments, the solid form comprises or consists essentially of a single printable composition.

Suitably, the printable composition(s) (and therefore the solid form) comprise the aforementioned carrier material. Suitably the carrier material is or comprises a meltable component. Suitably the "meltable" component is a component that melts (or undergoes a glass transition to thereby soften) at the designated operating temperature of any corresponding 3D printer extrusion nozzle configured to process said printing composition or filament. Suitably, the "meltable" component may be a mixture of components, which collectively melt or undergo glass transitions together as a mixture—e.g. carrier polymer and plasticizers. Suitably the meltable component has a melting point (or $T_g$) at or below 220° C., suitably at or below 150° C., suitably at or below 100° C., suitably at or below 80° C., suitably at or below 60° C. Suitably the meltable component has a melting point (or $T_g$—i.e. at least one $T_g$) greater than or equal to 20° C., suitably greater than or equal to 30° C., suitably between 30 and 65° C., suitably between 30 and 35° C.

As explained above, references to "meltable" components encompasses "softenable" components, where instead of "melting" at a particular temperature the component "softens". As such, references in this context to a melting point may additionally or alternatively relate to a glass transition temperature. Such glass transitions are particularly applicable to thermoplastic component(s). As such, a "meltable" component may be a thermoplastic component, suitably whose glass transition temperature (temperature at which the thermoplastic component softens rather than melts) is lower than the temperature to which said component is exposed (e.g. during printing).

For instance, typically the melting component is a carrier polymer, such as an carrier material, and is suitably selected to undergo melting or a glass transition during 3D-printing. Suitably this characteristic glass transition temperature is measurable using the well-known techniques described herein and elsewhere, and is a consequence of the combination of ingredients.

The solid form may comprise various concentrations of the carrier material or meltable component. Suitably, the weight ratio of carrier material (or meltable component) to other (potentially non-meltable) components of the solid form is between 1:10 and 10:1, more suitably between 3:7 and 7:3, suitably between 4:6 and 6:4, where suitably the meltable component(s) collectively include all relevant meltable components (e.g. carrier polymers, plasticizers, etc.) and other (non-meltable component(s)) include all relevant non-meltable components (e.g. filler(s), lubricants, active ingredient(s), etc.). Suitably the active ingredient is itself a non-meltable component.

Suitably, solid forms of the invention comprise greater than or equal to 10 wt % carrier material (suitably excluding any plasticizer(s)), suitably greater than or equal to 20 wt %, suitably greater than or equal to 30 wt %, suitably greater than 50 wt %, suitably greater than or equal to 79 wt %. Suitably, solid forms of the invention comprise less than or equal to 99 wt % carrier material (suitably excluding any plasticizer(s)), suitably less than or equal to 90 wt %, suitably less than or equal to 80 wt %, suitably less than or equal to 60 wt %. In a particular embodiment, the solid form comprises 40-60 wt % carrier material, suitably 45-55 wt %.

Suitably, solid forms of the invention comprise greater than or equal to 0.1 wt % plasticizer(s), suitably greater than or equal to 1 wt %, suitably greater than or equal to 4 wt %, suitably greater than 9 wt %. Suitably, solid forms of the invention comprise less than or equal to 50 wt % plasticizer (s), suitably less than or equal to 30 wt %, suitably less than or equal to 15 wt %, suitably less than or equal to 11 wt %.

Suitably the combined concentration of carrier material(s) and plasticizer(s) is between 30 and 80 wt %, suitably between 40 and 60 wt %, most suitably between 45 and 55 wt % of the solid form.

Suitably, solid forms of the invention comprise one or more fillers, where a filler is suitably a different component to any carrier material(s). The one or more fillers are suitably selected from organic or inorganic compounds, suitably compounds having a melting point of at least 150° C., suitably at least 200° C., suitably at least 500° C., suitably at least 1000° C. The one or more fillers are suitably fillers approved for pharmaceutical and/or nutraceutical use, or are at least GRAS approved. Suitably the one or more fillers constitute or form a part of a non-melting or non-meltable component of a solid dosage form (which suitably refers to the component's meltability under prevailing 3D printing conditions). Suitably the solid form (and/or filament) comprises at least 10 wt % filler(s), suitably at least 25 wt % thereof, more suitably at least 40 wt % thereof. Suitably the solid form comprises no more than 70 wt % filler(s), suitably no more than 60 wt % thereof. The presence of fillers can significantly improve the structure of printing compositions, such as filaments, and also any resulting printed solid forms, and can also facilitate printing itself, especially where the filler(s) are non-melting (or do not undergo any glass transitions) within a heated extrusion nozzle.

Any active ingredient is suitably distributed (substantially) uniformly within the carrier material (or meltable component(s)).

The solid form itself suitably has a glass transition temperature ($T_g$) between 20 and 200° C., suitably between 45° C. and 165° C., or suitably between −10° C. and 165° C. Suitably the solid form has a glass transition temperature ($T_g$) between 30 and 65° C. In an embodiment the solid form has a glass transition temperature between 30 and 35° C.

Suitably, the composition of the solid form is judiciously tailored with appropriate proportions and types of carrier material(s) to allow for the use of appropriate printing compositions (such as filaments) with a desired $T_g$ and/or melting point to minimise the corresponding nozzle operating temperature required for extrusion.

Active Ingredient

The present invention is suitably applicable for use with solid dosage forms comprising any active ingredient.

The active ingredient is most suitably a pharmaceutical drug substance (which may be any suitable pharmaceutical compound or pharmaceutically acceptable salt, solvate, prodrug, or polymorph thereof). As such, any carriers, diluents, and/or excipients used within the active ingredient-containing printing filament, or indeed any further printing filaments that may be used in the manufacture of a corresponding solid dosage form, are suitably pharmaceutically acceptable carriers, diluents, and/or excipients.

The active ingredient is suitably in the same form as the active ingredient is in approved drug products. The active ingredient is suitably in the same form (and has substantially the same purity) as the active ingredient before it is incorporated into the filament.

In a particular embodiment, the active ingredient is very soluble, freely soluble, or soluble in accordance with the standard USP (United States Pharmacopeia) definitions for solubility. In another embodiment, the active ingredient is sparingly soluble, slightly soluble, or very slightly soluble in accordance with the standard USP definitions for solubility.

In a particular embodiment, the active ingredient is very soluble in accordance with the standard USP definitions for solubility.

In a particular embodiment, the active ingredient is freely soluble in accordance with the standard USP definitions for solubility.

In a particular embodiment, the active ingredient is soluble in accordance with the standard USP definitions for solubility.

In some embodiments, the active ingredient is sparingly soluble in accordance with the standard USP definitions.

In some embodiments, the active ingredient is slightly soluble in accordance with the standard USP definitions.

In some embodiments, the active ingredient is very slightly soluble in accordance with the standard USP definitions.

In some embodiments, the active ingredient is practically insoluble in accordance with the standard USP definitions.

The active ingredient suitably has a higher melting point than the melting point or glass transition temperature (softening temperature) of the solid form.

The active ingredient suitably has a higher melting point than the melting point or glass transition temperature (softening temperature) of the carrier material(s).

Suitably, the active ingredient has a melting point greater than or equal to 150° C., more suitably greater than or equal to 190° C., more suitably greater than or equal to 250° C.

The same parameters suitably apply where the solid dosage form is a nutraceutical or food supplement solid dosage form.

Applications of Solid Form

The solid form of the invention may take a variety of forms, though most suitably the solid form is a solid dosage form, most suitably a solid dosage form of a pharmaceutical, nutraceutical, or food supplement composition.

In a particular embodiment, the solid dosage form is a pharmaceutical composition.

In a particular embodiment, the solid dosage form is a solid dosage form for use in the manufacture of a medicament. Suitably the solid dosage form is a solid dosage form for use in therapy.

The present invention also provides a method of treating a disease, condition, or disorder in a subject in need of such treatment. The method suitably comprises administering a therapeutically effective amount of the solid dosage form to the subject. Suitably the subject is an animal or human subject, most suitably a human subject.

Most suitably, the solid form is an immediate release pharmaceutical solid dosage form for oral administration.

Method of Preparing Solid Form and Relevant Printing Apparatus

The present invention provides a solid form printing apparatus for printing a solid form, the apparatus comprising:
 a 3D printer;
 a build platform upon which the solid form is printable (i.e. upon which the solid form may be built);
 a body printing composition or filament comprising a carrier material (suitably as defined herein);
 optionally a channel printing composition or filament comprising a channel material (suitably as defined herein); and
 a computer for controlling the 3D printer and optionally also the build platform.

(wherein the 3D printer is suitably operable via the computer, suitably a computer running pursuant to specialist solid form printing software, and optionally also to one or more databases, to print the solid form upon the build platform, suitably via a process involving the printing and/or extrusion of the relevant composition(s) or filament(s) to produce a solid form comprising one or more channel(s), wherein the channel(s) comprise void space and/or a channel material).

The printing apparatus suitably allows the printing of a solid dosage form (e.g. tablet or implant) via fused filament fabrication (FFF). The apparatus suitably comprises a fused filament fabrication 3-dimensional printer (an FFF 3D printer). Such printers are often referred to as fabrication deposition modelling™ (FDM) 3D printers.

Suitably, the apparatus comprises at least one extrusion nozzle through and from which a printing composition or filament (or part thereof) can be extruded. Suitably the or each extrusion nozzle may be a heated extrusion nozzle, suitably a heated extrusion nozzle with a variable temperature control (e.g. to allow the extrusion nozzle to be selectively heated at a desired temperature). As such, the apparatus may comprise an extrusion nozzle heating element, suitably for heating the extrusion nozzle to melt, soften, or otherwise liquidise the or part of the relevant composition or filament. Suitably, the apparatus may comprise a plurality of the aforementioned extrusion nozzles, each of which may be assigned to one or more compositions or filaments.

Suitably, the printing apparatus comprises a conveyor for conveying the printing composition(s) or filament(s) to and/or through the at least one extrusion nozzle.

Suitably, the operating temperature of an extrusion nozzle through which relevant printing composition(s) and/or filament(s) pass is high enough to enable extrusion but low enough to avoid unacceptable degradation of any relevant active ingredient(s) and/or any excipient(s) at the relevant filament feed rate (it will be appreciated by those skilled in the art that the active ingredient will generally tolerate higher temperatures if heat exposure times are short, as they generally are in the printing processes of the invention). Suitably, the operating temperature of an extrusion nozzle through which relevant printing composition(s) and/or filament(s) pass is between 90 and 220° C., more suitably between 120 and 190° C., suitably between 165 and 190° C. However, the operating temperature of an extrusion nozzle may be as low as 65° C., especially in systems that employ low-melting carrier polymers (e.g. PEG) or polymers with low glass transition temperatures. Most suitably, the extrusion nozzle temperature is set to at least 65° C., more suitably at least 70° C. In a particular embodiment, the nozzle temperature is 70-220° C., suitably 100-160° C., suitably 130-150° C., suitably 135-145° C.

Suitably each extrusion nozzle comprises an input opening (into which a filament is fed) and an output opening (out of which molten filament is deposited). The output opening is suitably smaller than the input opening. The input opening is suitably dimensioned to receive a corresponding printing composition or filament therethrough. Suitably the input opening has a diameter of 1.0 to 2.5 mm, more suitably 1.5 to 2.0 mm, most preferably about 1.75 mm. The output opening is suitably dimensioned for the properties of the corresponding printing composition or filament to allow molten composition or filament to be deposited therefrom (e.g. onto a build platform). Suitably the output opening has a diameter of 50 to 400 μm, more suitably 100 to 300 μm, more suitably 150 to 250 μm, most suitably about 200 μm. In an embodiment, the nozzle has an output opening with a diameter between 200 and 500 μm.

Suitably the or each nozzle may be movable (suitably in an automated fashion or in a manner controlled by a computer or by the printer under instruction from the computer) to extrude filament at different locations upon the build platform (or upon the partially formed solid dosage form printed thereon). The nozzle may be moveable in any or all of the X, Y, and Z direction, though in some embodiments (e.g. where the build platform is movable in the Z direction, i.e. up and down relative to the nozzle) it is constrained to move in only X and Y directions.

Suitably the or each extrude nozzle is operable to move at a speed of between 50 and 150 mm/s whilst extruding (i.e. when the nozzle is "on" —may be the nozzle extrusion speed), more suitably between 70 and 110 mm/s, more suitably between 80 and 100 mm/s. Suitably the or each extrude nozzle is operable to move at a speed of between 100 and 200 mm/s when not extruding (i.e. when the nozzle is "off"—this may be the nozzle travelling speed), more suitably between 120 and 180 mm/s, more suitably between 140 and 160 mm/s.

It will be understood by those skilled in the art that the, each, or any nozzle may be adapted to suit the properties a corresponding filament configured to print thereto. The nozzle properties/design and filament properties/composition suitably complement one another so as to facilitate controlled extrusion of said filament (be it continuous or intermittent, e.g. where more than one filament is used in the printing of a solid form), suitably without any nozzle blockages or impedence, and suitably without any unacceptable degradation of ingredients within the printing composition or filament during the printing process.

Suitably, during printing (e.g. at the relevant printing operating temperature), the surface of the build platform onto which the solid dosage form is to be printed adheres to the solid form (or at least to the layer thereof in contact with the build platform) sufficiently to prevent movement of the developing solid form during printing. Suitably, however, after printing (e.g. optionally at a different temperature to the printing operating temperature) the printed solid form(s) may be removed from the build platform without being damaged (e.g. the build platform is non-adherant enough to allow the solid forms to be removed or is selectively tunable, e.g. by changing the operating temperature, to allow the solid dosage forms to be removed therefrom). As such, the surface of the build platform may comprise a surface coating or surface tape which imparts the required surface properties (e.g. adhesive but not too adhesive that the solid forms are permanently adhered).

The build platform is suitably configured or operable to maintain a surface temperature (i.e. for the surface in contact with the solid dosage form) during printing of less than or equal to 50° C., suitably less than or equal to 40° C., suitably less than or equal to 30° C., suitably greater than or equal to 5° C., suitably greater than or equal to 15° C. In other embodiments, the build platform is operable to maintain a surface temperature of less than or equal to 150° C., suitably less than or equal to 100° C., suitably greater than or equal to 15° C. This may be achieved through selective operation of heating and/or cooling elements associated with (e.g. lying beneath) the surface of the build platform. In a particular embodiment, the build platform is operable and preferably operated to maintain a surface temperature of between 20 and 90° C., suitably between 20 and 60° C., suitably between 30 and 50° C., most suitably about 40° C.

The build platform may be movable (suitably in an automated fashion or in a manner controlled by a computer or by the printer under instruction from the computer) to control the position or height of extrusion of a relevant filament upon the build platform. The build platform may be moveable in any or all of the X, Y, and Z direction, though in some embodiments the build platform is movable in the Z direction only, i.e. up and down. Movement in the Z direction allows the gap (or height) between the nozzle and the printing point to be kept substantially constant throughout the printing process to maintain layer-by-layer consistency.

Suitably the computer is configured (suitably when running pursuant to solid form printing software of the invention) to print the solid form in a fashion to leave channels of either or both void space and/or channel material. The computer may thus be configured to operate the 3D printer pursuant to a pre-determined solid form design pattern.

Conventional FFF 3D printers are well known in the art, and are generally suitable for use with the present invention, though they may be judiciously modified based on the principles outlined herein to optimise printing of solid dosage forms. For the skilled persons reference, the following research articles describe a viable operation of FFF 3D printers—S. H. Masood, "Application of fused deposition modelling in controlled drug delivery devices", *Assembly Automation,* 27/3 (2007), p.215-221 and Khaled et al, "Desktop 3D printing of controlled release pharmaceutical bilayer tablets", *International Journal of Pharmaceutics*, 461 (2014), p.105-111—describe printing with FFF 3D printers of filaments, albeit there are no active ingredients contained within the filaments being printed (drug compounds are infused at a later stage). Suitably in the present invention drug compounds are formulated within printing composition(s) or filament(s) and printed directly as a solid dosage form.

The present invention provides a method of preparing (or printing) a solid form, the method comprising:
a) providing a solid form printing apparatus, the apparatus comprising:
  a 3D printer (suitably an FFF 3D printer);
  a build platform upon which the solid form is printable;
  a body printing (ink, or filament) composition comprising a carrier material optionally mixed with one or more additional ingredients (e.g. a pharmaceutical active);
  optionally a channel printing (ink, or filament) composition comprising a channel material optionally mixed with one or more addition ingredients (e.g. a pharmaceutical active);
  optionally a computer for controlling the 3D printer and optionally also the build platform;
b) operating the 3D printer to print the solid form upon the build platform via a process (suitably a computer-implemented method) comprising:
  i) printing (and/or extruding) the body printing composition to form the or part of a body of the solid form; and either
    I. leaving channels of void space(s) within the body or surface of the solid form; or
    II. optionally printing (and/or extruding) the channel printing composition to form channels of channel material within the body or surface of the solid form;
c) optionally performing one or more further processing steps (with or without the 3D printer; e.g. coating or otherwise modifying the surface, shape, or properties of the solid form).

The present invention also provides a method of printing a solid form, suitably as defined herein. Suitably this method is a method of using the aforesaid apparatus. Suitably the solid form is printed pursuant to a pre-designated design uploaded to the computer, suitably via the computer software.

The present invention also provides a solid form (e.g. a solid dosage form as defined herein) obtainable by, obtained by, or obtained directly by the process (or computer-implemented method) of preparing a solid form, suitably as afore-described.

The method suitably involves operating the printing apparatus via a computer, which is suitably connected (be it in a wired or wireless fashion) with or within the relevant printing apparatus (so as to allow the computer to control and co-ordinate other parts of the apparatus, suitably including an FFF 3D printer), to cause printing of a solid form.

Depending on the shape and dimensions of the solid form to be printed, sacrificial supports or rafts (which can be removed after fabrication of the solid dosage form(s), e.g. by dissolving them after printing) may be used during printing. Such sacrificial supports or rafts are suitably themselves printed from corresponding filament(s). However, in preferred embodiments, no such supports or rafts are required.

According to a further aspect of the present invention, there is provided a computer for operating a solid form printing apparatus, a fused filament fabrication (FFF) 3D printer, or printing apparatus, wherein the computer comprises:
an interface connecting or enabling connection of (whether wirelessly or wired) the computer to or within a solid form printing apparatus, a fused filament fabrication (FFF) 3D printer, or printing apparatus (suitably to allow the computer to control and/or operate the aforesaid);
wherein the computer runs pursuant to solid form printing software (and optionally also to one or more databases), which configures the computer to carry out the steps of:
  i) obtaining information (e.g. through manual user input or via one or more databases, optionally in response to a user-inputted reference, such as a patient's name) regarding one or more parameters pertaining to the solid form to be printed (e.g. the active ingredient, active loading/dose, shape, release profile, etc.);
  ii) calculating the mass and/or volume of the solid form to be printed based on the information obtained in step (i);
  iii) controlling printing of and relative proportions of ingredients within (i.e. make up of the solid dosage form) the solid form by, on the basis of the information obtained in step (i) and calculations performed in step (ii):
    a. controlling printing, deposition, and/or extrusion, of a body printing composition;
    b. optionally controlling printing, deposition, and/or extrusion, of a channel printing composition;
    c. optionally controlling performance of one or more further processing steps).

According to a further aspect of the present invention, there is provided a computer-implemented method of operating a solid form printing apparatus, a fused filament fabrication (FFF) 3D printer, or printing apparatus as defined herein, the method comprising:
operating a computer (with suitable data connections to the relevant printing apparatus, be them wired or wireless) running pursuant to solid form printing software (and optionally also to one or more databases) to:
  i) obtain information (e.g. through manual user input or via one or more databases, optionally in response to a user-inputted reference, such as a patient's name) regarding one or more parameters pertaining to the solid form to be printed (e.g. the active ingredient, active loading/dose, shape, release profile, shape, colour, etc.);
  ii) calculate the mass and/or volume of the solid form to be printed based on the information obtained in step (i);
  iii) control printing of and relative proportions of ingredients within (i.e. make up of the solid form) the solid form by, on the basis of the information obtained in step (i) and calculations performed in step (ii):
    a. controlling printing, deposition, and/or extrusion, of a body printing composition;
    b. optionally controlling printing, deposition, and/or extrusion, of a channel printing composition;
    c. optionally controlling performance of one or more further processing steps).

The computer associated or otherwise connected with the printing apparatus suitably controls printing of the relevant printing composition(s) or filament(s) in accordance with a solid form design and/or solid form parameters (e.g. relative amounts and juxtaposition of ingredients, channels, etc.) set forth in a given solid dosage form data file (e.g. in a CAD or a .STL file), suitably as interpreted by relevant software pursuant to which the computer runs.

In a particular embodiment, especially where the printing apparatus is configured to print pharmaceutical, nutraceutical, or food supplement solid dosage forms, the printing apparatus comprises or is connected to a local computer, and both printing apparatus and the local computer are located on site at a pharmacy, most suitably in a purpose-build printing area or room (which may be suitably have regulatory approval).

Suitably, a computer running pursuant to said to solid dosage form printing software is configured to calculate the mass and/or volume of the solid dosage form to be printed based on the information obtained. Suitably once the computer has obtained all required information (be it information manually inputed by a user, information imported automatically, or a combination of both) it is configured to perform calculations to allow finalisation of printing instructions before the computer controls printing. At this stage, further input may be required or requested (e.g. via a user interface), for instance dimension(s) and/or shape modifications may be optionally selected. Calculations typically relate to the mass and/or volume of a given solid dosage form required to provide a given active dosage per dosage form. Though it may be possible to increase the concentration of a given active relative to other ingredients (e.g. excipients), typically formulations are optimised and relative proportions fixed/pre-set, whereas overall mass/volume may be varied whilst retaining the same relative proportions of ingredients.

The computer may also be configured to perform calculations based on disintegration and/or solubility properties of a given solid form so as to customise the printing (or leaving) of channels within the body or surface of the solid dosage form.

According to a further aspect of the present invention, there is provided a computer program, comprising solid form printing software code for performing the computer-implemented method defined herein when the computer program is run on a computer.

According to a further aspect of the present invention, there is provided a computer-readable medium comprising solid form printing software code executable of cause a computer to perform the computer-implemented method defined herein when the software code is executed on a computer.

EXAMPLES 1.1 Materials and Equipment

Eudragit E PO was donated by Evonik Industries (Darmstadt, Germany). Triethyl citrate (TEC) and Hydrochlorothiazide were supplied by Sigma-Aldrich (UK). Scotch blue painter's tape 50 mm was supplied by 3M (Bracknell, UK).

MakerBot Replicator® 2×Experimental 3D Printer (MakerBot Industries, LLC, New York, USA) was utilized to print all the relevant tablets. The 3D Printer was, where relevant, modified as described below.

Example 1—General Procedure for Preparing FFF 3D-Printable Filaments based on a Hydrochlorothiazide Active Ingredient Carried within a Eudragit E PO Carrier Polymer In previous experiments conducted by the inventor, the feasibility of using different excipients with 3D printers was examined by inter alia producing filaments with various different fillers. Such filaments were first extruded out through HAAKE MiniCTW (Karlsruhe, Germany). The filaments first contained a particular ratio of polymer/plasticiser and fillers. Once a specific ratio was determined the drug was then incorporated into the filament.

The powders were first accurately weighed and mixed before feeding into a counter flow twin screw system in order to integrate all the ingredients uniformly. The parameters used for filament making were, 90 rpm for melting the powder and mixing thereafter, before extrusion, at 100° C. The extrusion temperature was kept 10° C. less than the mixing and feeding temperature as it affects the nature of the filament made. The die nozzle size varied according to formulation and the excipients involved as it affects the diameter of filament and hence compatibility with 3D printers. The standard diameter however was 1.25 mm which proved to be making compatible filaments with 3D printers. The torque control for extrusion was 0.8 Nm. After making filaments, they were kept in sealed plastic bags to be used in 3D printers afterwards. Once the working ratio was optimised for polymer, plasticiser and fillers, the filaments containing drugs were then made to be tested for different pharmacopoeia's standards.

3D-printable filaments were prepared via a hotmelt extrusion process. This process generally involved first mixing the relevant ingredients (e.g. drug, carrier(s), and optional plasticizer) within a hotmelt extruder at an appropriate temperature ($T_1$—mixing temperature) to suit the mixture in question (i.e. to allow for fluid mixing) to give a substantially uniform mixture, before the mixture was then extruded through a heated filament-forming nozzle (having the desired size/diameter, $N_1$) at an appropriate temperature ($T_2$—processing temperature) to suit the mixture and to achieve a desirable torque. Filaments were extruded from the filament-forming nozzle using counter-flow extruders which rotate at an appropriate speed to yield filaments having the desired properties. Filaments were typically dispensed onto a Teflon™ coated surface and stored in a plastic back prior to their use in 3D printing.

Generally about 7 g (total preparation mass) of the preparation was accurately weighed—for instance to achieve the following ratio:

| Drug | Ca.Tri.Phosphate | EPO | TEC | Filament Diameter |
|---|---|---|---|---|
| Model drug 12.5% | 37.5% | 46.75% | 3.25% | 1.25 mm | where the model drug was hydrochlorothiazide, Ca.Ti.Phosphate is calcium tribasic phosphate, EPO is Eudragit E PO (the carrier polymer), and TEC is triethylcitrate (a plasticizer).

The resulting weighed preparation was then manually loaded to a HAAKE MiniCTW hotmelt extruder, wherein the preparation was allowed to mix at an appropriate mixing temperature ($T_1$—typically 100° C.) to suit the mixture and allow for substantial homogenisation for at least 5 minutes prior to extrusion. The counter flow extruders rotation speed was set at 90 rpm. Once properly mixed, the mixture was extruded from a heated filament-forming nozzle at an extrusion temperature ($T_2$—typically 100° C.) suitable to achieve a torque of approximately 0.6 Nm/screw (extrusion temperature $T_2$ is typically 10 lower than preparation temperature, $T_1$- i.e. $T_1$-$T_2$=between 20 and 30). Extrusions were carried out using different nozzle sizes (0.5-2.0 mm, in these experiments 1.25 mm was used) using torque control of 0.6

Nm/screw. The extrudes were received on Teflon coated conveying belt and stored in plastic bag until it is used as a filament for 3D printing.

For Eudragit® E PO, the operating temperature in HME is general set between 100° to ° C. (105° in most cases).

Where a drug is present, the resulting filaments general display a substantially uniform distribution of the drug within the carrier/polymer matrix. Drug-loadings within the filament were generally 10 wt % and above, and generally 60 wt % and below.

The target diameter of the filaments (i.e. their thickness) was approximately 1.75 mm, since this diameter is most compatible with the 3D printer being used.

After hot extruding the polymer into a filament, they were used as a filament (ink) for 3D printing of tablets.

Specific examples and results relating to both filaments and printed dosage forms are presented below. However, the following ingredients were employed in the formation of the aforesaid filaments:

| Drug | Ca.Tri.Phosphate | EPO | TEC | Diameter |
|---|---|---|---|---|
| Model drug 12.5% | 37.5% | 46.75% | 3.25% | 1.25 mm |

Example 2—Tablet Design

Tablets as detailed herein were designed using Autodesk® 3ds Max® Design 2012 software version 14.0 (Autodesk, Inc., USA) and saved in STL format.

The design was imported to the 3D printer's software, MakerWare Version 2.4.0.17 (Makerbot Industries, LLC., USA). A series of tablets were printed with the pre-designated dimensions of the design: length×width×heights (L, H, W). Relevant dimensions for the various model studies are described further below.

A series of tablets containing hydrochlorothiazide and Eudragit E PO were printed with and without channels, Example 3—General Modifications of 3D Printer Default settings of the printing software were as follows: type of printer: Replicator 2×; type of filament: PLA; resolution: standard; temperature of nozzle: 135° C.; temperature of building plate: 20° C.; speed of extruder 90 mm/s while extruding and 150 mm/s while traveling; infill: 100%; height of the layer: 200 µm; number of shells: 2. No supports or rafts were utilized in the printing process. No further modifications were implemented.

Before printing tablets, the following modifications of the 3D printer were implemented:
 a) The default Kapton tape layer provided poor adhesion to the designs to the build platform. As such, this tape was replaced by blue Scotch painters tape applied to the surface of the build platform to improve adhesion to the surface layer.
 b) The 3D printer was modified to introduce a plasticizing station upstream from (i.e. before) the filament feed into the extrusion nozzle. To enable printing of theophylline loaded tablets the following changes in setting were made: temperature of nozzle: 135° C.; temperature of building plate: 40° C. Speed of extruded remained the same with more detailed settings added: bridges print speed: 40 mm/s; first layer print speed: 30 mm/s; infill print speed: 90 mm/s; insets print speed: 90 mm/s; outlines: 40 mm/s. Type of the filament, resolution, infill, height of the layer were not changed.

Example 4—General Procedure for Dissolution Studies

Dissolution patterns of tablets were observed using USP II dissolution apparatus with 750 ml HCl and at rotation speed of 50 rpm. Dissolution times were recorded based on when complete drug dissolution was visually observed.

Example 5—General Procedure for Disintegration Studies

Disintegration tests were generally performed to determine whether tablets disintegrate in a prescribed period of time. The examination was conducted in accordance with British Pharmacopeia. Disintegration test for tablets was carried out in a basket rack assembly having 6 cylinders inside. A volume of 750 ml 0.1 M HCl was taken in each cylinder. The time and temperature were set to 37° C. and 15 minutes respectively. The tablets prior to test were weighed accurately. The exact time was noted for the tablets at which they were disintegrated. Disintegration test for drugs was carried out with six tablets each.

Results and Experiments

1. Identification of Dissolution Rates for Eudragit E-based Tablets

The dissolution rate of tablets was found to be dependant of the size of the tablet, and it was noted that in certain circumstances, and for certain tablet sizes, the USP and other Pharmacopeia requirements for immediate release may not be satisfied. As shown in FIG. 1, tablets formulated for the current studies which were larger than 12 mm in length would fall short of the immediate release requirements.

FIG. 1 shows % drug (hydrochlorothiazide) release profiles over time based on in vitro dissolution tests for standard-formulated unchannelled 3D-printed Eudragit E PO-based tablets of varying length dimensions (L=6, 9, 12, 14, 16, 18 mm).

2. Initially-Proposed Model Studies for Modifying Tablets Designs to Improve Dissolution Rates of Tablets The following strategies were adopted in an attempt to accelerate drug release from solid drug design:
 D1 (Design strategy I): Tablets with square shaped channels of varying size.
 D2 (Design strategy II): Tablets with rectangular channels of varying size.
 D3 (Design strategy III): Tablets with radiator-like channels of varying size.
 D4 (Design strategy IV): Tablets containing weak-joint structures.

D1: Tablets with Square Shaped Channels of Varying Size

This strategy involved the introduction of 9 square-shaped channels of varying size into the long side of the tablets, but was also extended to involve introduction of 18 square-shaped channels of varying size into the short side of the tablets. Table 1 below shows the dimensions (in mm) of the tablets (X, Y, Z dimensions), the relevant solid volumes in $mm^3$ $V_{sol}$) (i.e. volumes of solid excluding the volume of any channels), relevant surface area in $mm^2$ ($A_{tot}$), calculated surface/volume ratios (S/V) or "solid-volume-based surface area density" in $mm^{-1}$, and relevant channel sizes (mm), where the channel size is the length of the shorted dimension of the channel (i.e. in this case the length of the side of the square characterising the relevant channel cross-section).

TABLE 1 dimensions, volume, surface area, and S/V for tablets with different corridor size of square channelled tablets.

| Tablet | X (mm) | Y (mm) | Z (mm) | Volume (mm$^3$) | Surface area (mm$^2$) | s/v (mm$^{-1}$) | Channel size (mm) |
|---|---|---|---|---|---|---|---|
| inner-no holes | 17.185 | 6.805 | 6.249 | 553.81 | 377.8 | 0.68218342 | |
| 9 long channels | 17.185 | 6.805 | 6.249 | 548.02 | 493.34 | 0.90022262 | 0.2 |
| 9 long channels | 17.185 | 6.805 | 6.249 | 530.46 | 607.59 | 1.1454021 | 0.4 |
| 9 long channels | 17.185 | 6.805 | 6.249 | 501.38 | 718.64 | 1.43332403 | 0.6 |
| 9 long channels | 17.185 | 6.805 | 6.249 | 460.95 | 825.89 | 1.79171277 | 0.8 |
| 9 long channels | 17.185 | 6.805 | 6.249 | 408.25 | 934.75 | 2.28965095 | 1 |
| 18 long channels | 17.185 | 6.805 | 6.249 | 549.07 | 471.19 | 0.85816016 | 0.2 |
| 18 long channels | 17.185 | 6.805 | 6.249 | 534.81 | 561.53 | 1.04996167 | 0.4 |
| 18 long channels | 17.185 | 6.805 | 6.249 | 511.19 | 647.5 | 1.26665232 | 0.6 |
| 18 long channels | 17.185 | 6.805 | 6.249 | 478.44 | 728.17 | 1.52196723 | 0.8 |
| 18 long channels | 17.185 | 6.805 | 6.249 | 436.91 | 802.4 | 1.83653384 | 1 |

FIG. 2 shows (a) photographs; and (b) rendered images; of tablets (with the same overall volume X=17.185, Y=6.805, Z=6.249) with 9 built-in long channels with increasing square channels (0.2, 0.4, 0.6, 0.8 and 1.0 mm).

FIG. 3 shows % drug (hydrochlorothiazide) release profiles over time based on in vitro dissolution tests for the channelled 3D-printed Eudragit E PO-based tablets of FIG. 2.

Figure 4:
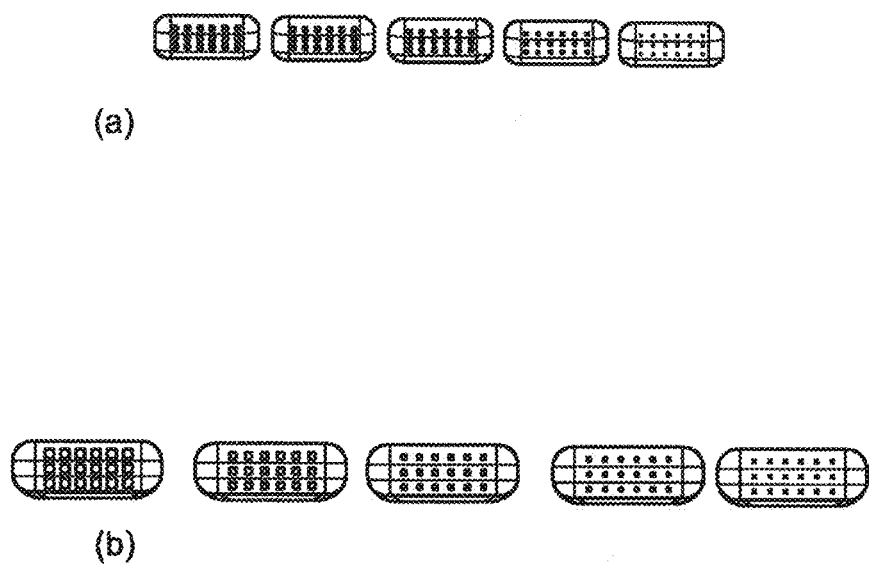
FIG. 4 shows (a) photographs; and (b) rendered images; of tablets (with the same overall volume X=17.185, Y=6.805, Z=6.249) with 18 built-in short channels with increasing square channels (0.2, 0.4, 0.6, 0.8 and 1.0 mm).

FIG. 4 shows (a) photographs; and (b) rendered images; of tablets (with the same overall volume X=17.185, Y=6.805, Z=6.249) with 18 built-in short channels with increasing square channels (0.2, 0.4, 0.6, 0.8 and 1.0 mm).

Figure 5:
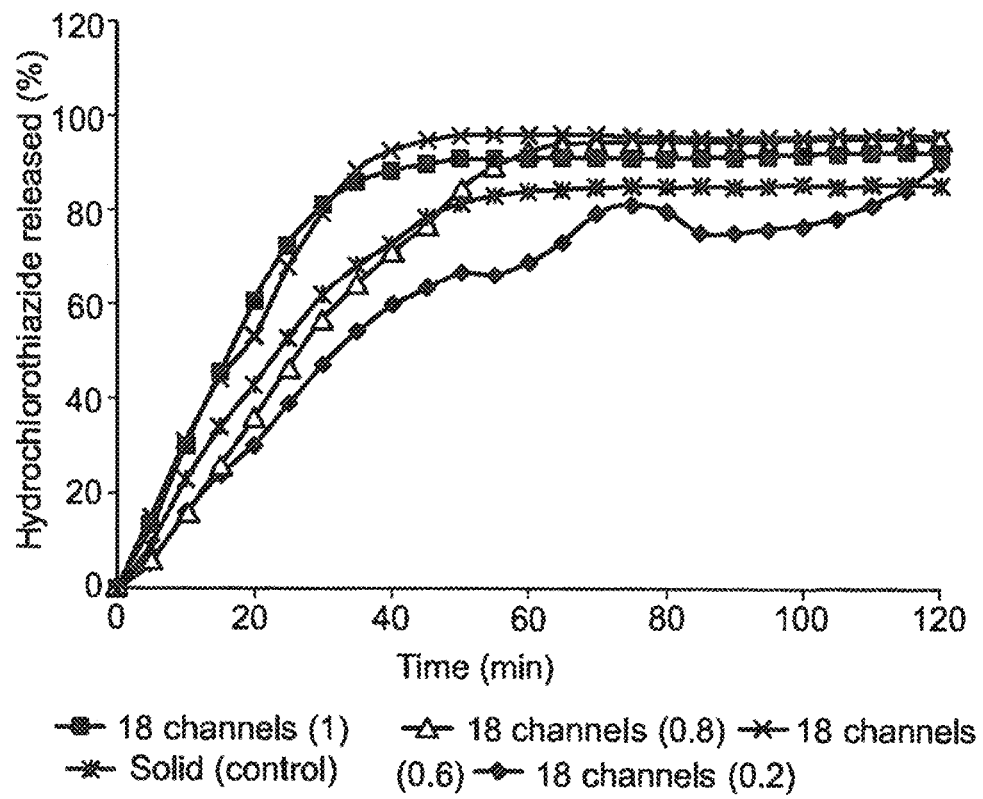
FIG. 5 shows % drug (hydrochlorothiazide) release profiles over time based on in vitro dissolution tests for the channelled 3D-printed Eudragit E PO-based tablets of FIG. 4 as compared to a solid control.

FIG. 5 shows % drug (hydrochlorothiazide) release profiles over time based on in vitro dissolution tests for the channelled 3D-printed Eudragit E PO-based tablets of FIG. 4.

It appears that channelled design have a higher dissolution rate than solid tablet (control). The dissolution rate was the highest for 0.8 and 1.0 mm channels for both 9-long channel and 18-short channels.

D2: Tablets with Rectangular Shaped Channels of Varying Size

This strategy involved the introduction of 3 rectangular-shaped channels (or corridors) of varying size into the long side of the tablets, but was also extended to involve introduction of 6 rectangular-shaped channels of varying size into the short side of the tablets. Table 2 below shows the dimensions (in mm) of the tablets (X, Y, Z dimensions), the relevant solid volumes in mm$^3$ ($V_{sol}$) (i.e. volumes of solid excluding the volume of any channels), relevant surface area in mm$^2$ ($A_{tot}$), calculated surface/volume ratios (S/V) or "solid-volume-based surface area density" in mm$^{-1}$, and relevant channel sizes (mm), where the channel size is the length of the shorted dimension of the channel (i.e. in this case the length of the shortest side of the rectangle characterising the relevant channel cross-section).

TABLE 2 dimensions, volume, surface area, and S/V for tablets with different corridor size.

| Tablet | X (mm) | Y (mm) | Z (mm) | Volume (mm$^3$) | Surface area (mm$^2$) | s/v (mm$^{-1}$) | Channel size (mm) |
|---|---|---|---|---|---|---|---|
| Inner-no holes | 18 | 7.13 | 6.548 | 637.29 | 414.87 | 0.65099091 | |
| 3 corridors | 18 | 7.13 | 6.548 | 606.16 | 742.65 | 1.22517157 | 0.2 |
| 3 corridors | 18 | 7.13 | 6.548 | 575.04 | 758.98 | 1.3198734 | 0.4 |
| 3 corridors | 18 | 7.13 | 6.548 | 543.94 | 774.94 | 1.42467919 | 0.6 |
| 3 corridors | 17.185 | 6.805 | 6.249 | 512.9 | 790.79 | 1.54180152 | 0.8 |
| 3 corridors | 17.185 | 6.805 | 6.249 | 481.91 | 806.51 | 1.67356975 | 1 |
| 6 corridors | 18 | 7.13 | 6.548 | 611.73 | 679.85 | 1.11135632 | 0.2 |
| 6 corridors | 18 | 7.13 | 6.548 | 586.17 | 689.22 | 1.17580224 | 0.4 |
| 6 corridors | 18 | 7.13 | 6.548 | 560.61 | 698.59 | 1.24612476 | 0.6 |
| 6 corridors | 17.185 | 6.805 | 6.249 | 535.05 | 707.96 | 1.32316606 | 0.8 |
| 6 corridors | 17.185 | 6.805 | 6.249 | 509.49 | 717.32 | 1.40791772 | 1 |

Figure 6:
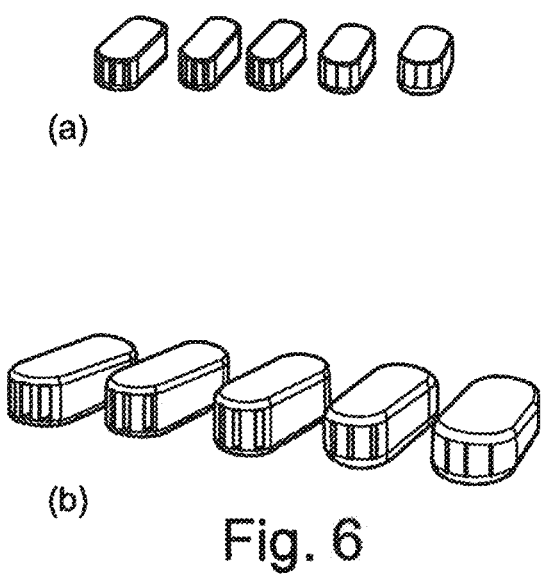
FIG. 6 shows (a) photographs; and (b) rendered images; of tablets (with substantially the same overall volume X=17.185, Y=6.805, Z=6.249) with 3 built-in long channels with increasing sized rectangle channels (0.2, 0.4, 0.6, 0.8 and 1.0 mm).

FIG. 6 shows (a) photographs; and (b) rendered images; of tablets (with substantially the same overall volume X=17.185, Y=6.805, Z=6.249) with 3 built-in long channels with increasing sized rectangle channels (0.2, 0.4, 0.6, 0.8 and 1.0 mm).

FIG. 7 shows % drug (hydrochlorothiazide) release profiles over time based on in vitro dissolution tests for the channelled 3D-printed Eudragit E PO-based tablets of FIG. 6.

FIG. 8 shows (a) photographs; and (b) rendered images; of tablets (with substantially the same overall volume X=17.185, Y=6.805, Z=6.249) with 6 built-in short channels with increasing sized rectangle channels (0.2, 0.4, 0.6, 0.8 and 1.0 mm).

FIG. 9 shows % drug (hydrochlorothiazide) release profiles over time based on in vitro dissolution tests for the channelled 3D-printed Eudragit E PO-based tablets of FIG. 8.

It appears that designs with 3 built-in corridors have much less effect on dissolution than the designs with 6 built-in corridors, which show a significant improvement on dissolution, especially for 0.8-1.0 mm sized channels.

D3: Tablets with Deep Grooved Radiator-Like Channels of Varying Size

This strategy involved the introduction of 8 deep-groove-shaped channels (or radiator-like channels) of varying size into the short side of the tablets. Table 3 below shows the dimensions (in mm) of the tablets (X, Y, Z dimensions), the relevant solid volumes in mm$^3$ ($V_{sol}$) (i.e. volumes of solid excluding the volume of any channels), relevant surface area in mm$^2$ ($A_{tot}$), calculated surface/volume ratios (S/V) or "solid-volume-based surface area density" in mm$^{-1}$, and relevant channel sizes (mm), where the channel size is the length of the shorted dimension of the channel (i.e. in this case the width of the groove or width of the shortest side of the substantially rectangular shape(s) characterising the relevant channel cross-section at each point).

TABLE 3

Dimensions, volume, surface area, and S/V for tablets with different corridor size.

| Tablet | X | Y | Z | Volume | Surface area | s/v | Corridor size (mm) |
|---|---|---|---|---|---|---|---|
| Inner- no holes | 18 | 7.13 | 6.548 | 637.29 | 414.87 | 0.65 | Inner- no holes |
| Lower base | 18 | 7.13 | 6.548 | 479.58 | 896.99 | 1.87 | 0.6 |

FIG. 10 shows (a) photographs; and (b) rendered images; of tablets (with substantially the same overall volume X=18, Y=7.13, Z=6.548) with 8 built-in deep-groove-shaped channels 0.6 mm in size (i.e. shortest dimension=width of the channel/groove).

Figure 11:
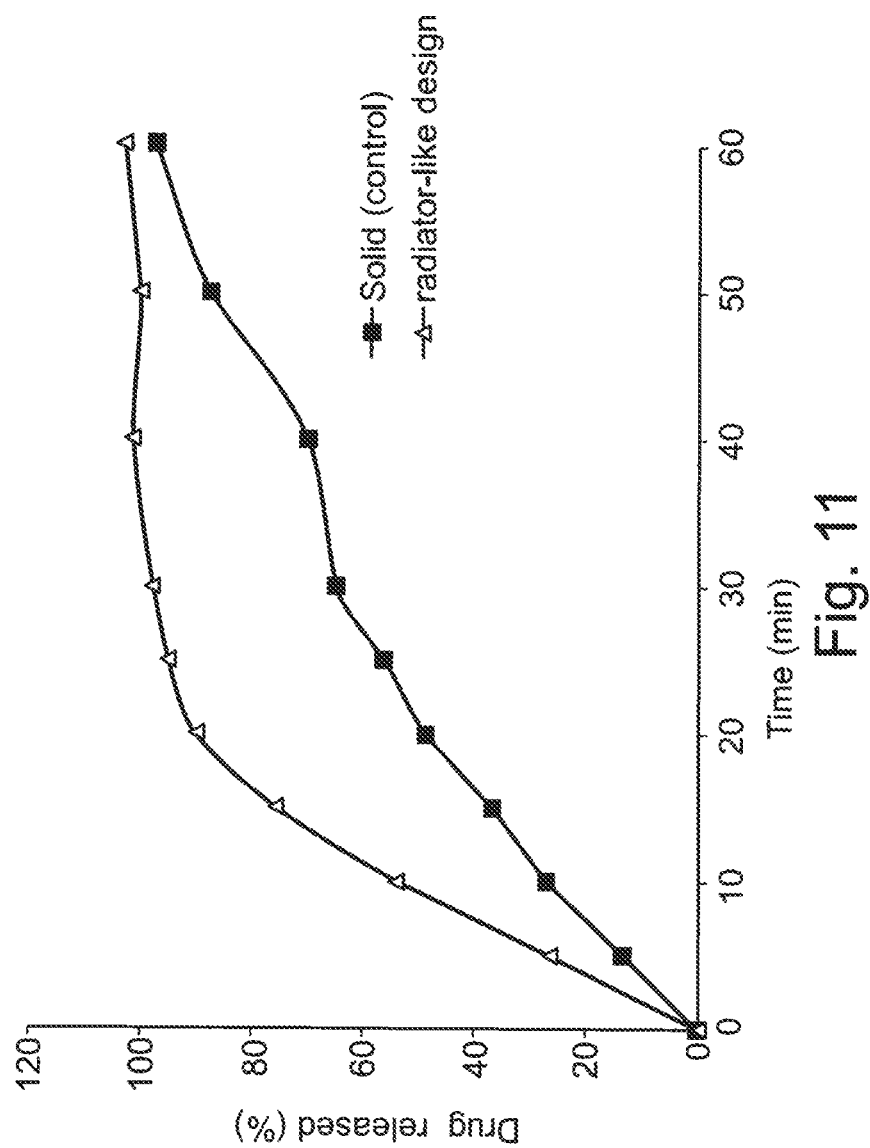
FIG. 11 shows % drug (hydrochlorothiazide) release profiles over time based on in vitro dissolution tests for the channelled 3D-printed Eudragit E PO-based tablets of FIG. 8, albeit with channels 1.0 mm in size as compared to a solid control.

FIG. 11 shows % drug (hydrochlorothiazide) release profiles over time based on in vitro dissolution tests for the channelled 3D-printed Eudragit E PO-based tablets of FIG. 8, albeit with channels 1.0 mm in size.

The radiator-like structure appears to have a significantly faster dissolution than the control.

D4: Tablets with Deep Grooves and Weak Points

This strategy involved the introduction of 7 deep-groove-shaped channels (or radiator-like channels, similar to those of D3) into the short side of the tablets, with bridging cross links (weak points).

Figure 12:
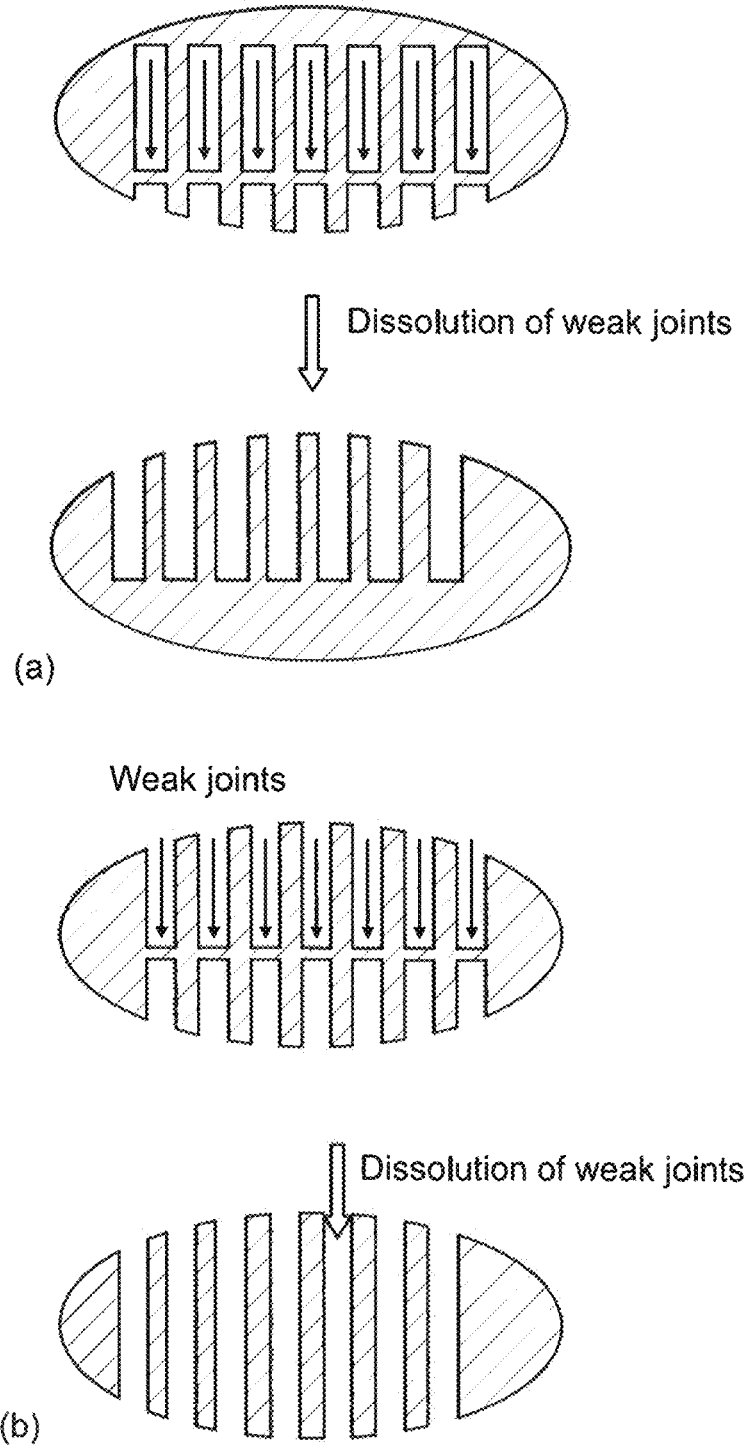
FIG. 12 shows (a) a side-cross section of a tablet design comprising 7 deep-groove-shaped channels with weak bridging cross-links; and (b) a side cross-section of a tablet design with sliced channels traversed by weak bridging cross-links.

FIG. 12 shows (a) a side-cross section of a tablet design comprising 7 deep-groove-shaped channels with weak bridging cross-links; and (b) a side cross-section of a tablet design with sliced channels traversed by weak bridging cross-links.

Figure 13:
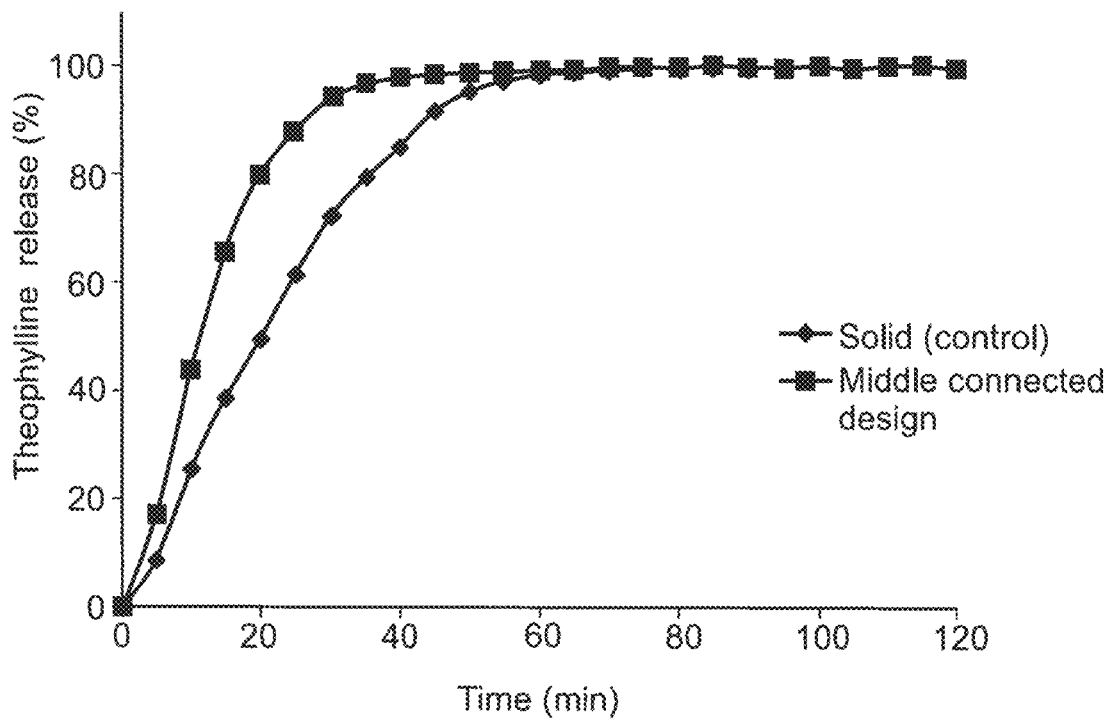
FIG. 13 shows % drug (theophylline) release profiles over time based on in vitro dissolution tests for the channelled 3D-printed Eudragit E PO-based tablets of FIG. 12, with channels of 0.6 mm in size as compared to a solid control.

FIG. 13 shows % drug (theophylline) release profiles over time based on in vitro dissolution tests for the channelled 3D-printed Eudragit E PO-based tablets of FIG. 12(a), with channels of 0.6 mm in size.

Table 4 below shows the dimensions (in mm) as per above.

TABLE 4

Dimensions, volume, surface area, and S/V for tablets with different corridor size

| Tablet | X | Y | Z | Volume | surface area | s/v | Space width (mm) |
|---|---|---|---|---|---|---|---|
| Inner- no holes | 18 | 7.13 | 6.548 | 637.29 | 414.87 | 0.65 | Inner- no holes |
| middle = connection | 18 | 7.13 | 6.548 | 479.17 | 908.58 | 1.896 | 0.6 |

The bridged design exhibited faster solubility than the control solid structure.

Further Examples

Figure 14:
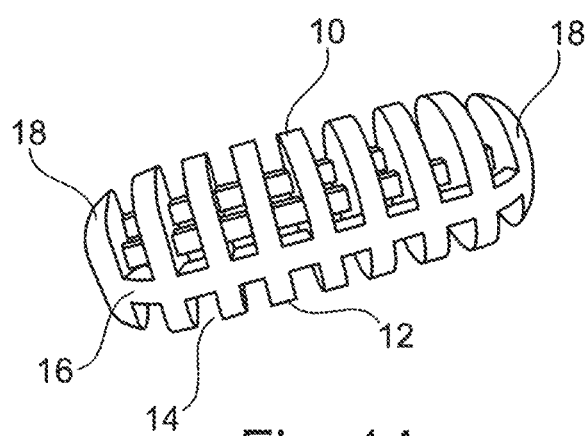
FIG. 14 shows the skelatal structure of 'Gaplet' tablets rendered with 3ds Max software.

A series of further dosage forms were prepared based on a common skeleton structure, as depicted in FIG. 14. As per Example 2 above, the dosage forms were initially designed using Autodesk® 3ds Max® Design 2012 software version 14.0 (Autodesk, Inc., USA) and saved in STL format.

FIG. 14 shows the skelatal structure of 'Gaplet' tablets rendered with 3ds Max software.

As can be seen, the dosage form (10) is characterised by a capsule-like shape, which is intended to be consumed (via oral administration) as a whole. However, the dosage form (10) itself essentially comprises a plurality of individual mini-dosage forms or dosage blocks (12) with a predefined shape (e.g. disc) interlinked, with pre-defined spaces (14) in between, by a series of bridging elements (16), capped at each end with end caps (18). The edged blocks (16) facilitate swallowing. In these embodiments, all solid elements are formed from the same material.

In this example, each individual bridging element is a member of one of three longitudinal bridges (16) extending either along one of two opposite sides of the dosage form or through the middle of the dosage form in a substantially coaxial fashion. Due to the position of a tablet during 3D printing, the bridges can be also referred to as upper, middle and bottom bridges.

Modifications of the number of bridges were undertaken and included printing tablets without the upper bridge, tablets without the middle bridge and tablets without two bridges, upper and middle. Decreasing the number of bridges was expected to facilitate the tablets breaking in the dissolution test, due to a weaker connection between the blocks.

Figure 15:
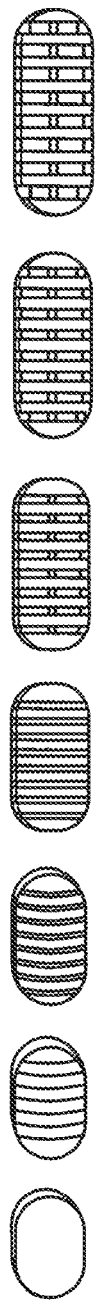
FIG. 15 shows further design images obtained from the 3ds Max software, with varying pre-defined spaces: 0, 0.2, 0.4, 0.6, 0.8, 1.0 and 1.2 mm. These tablets had 1.0 mm thick blocks with increasing spacing, respectively: 0, 0.2, 0.4, 0.6, 0.8, 1.0 and 1.2 mm spaces from left to right.

FIG. 15 shows further design images obtained from the 3ds Max software, with varying pre-defined spaces: 0, 0.2, 0.4, 0.6, 0.8, 1.0 and 1.2 mm. These tablets had 1.0 mm thick blocks with increasing spacing, respectively: 0, 0.2, 0.4, 0.6, 0.8, 1.0 and 1.2 mm spaces from left to right.

As per some of the previously-presented examples herein, such dosage forms break in situ (i.e. after being swallowed)

into multi-units causing the acceleration of drug release from the matrix tablets, enabling compliance with USP criteria for immediate-release products.

The design was imported to the 3D printer's software, MakerWare Version 2.4.0.17 (Makerbot Industries, LLC., USA) in order to print a series of tablets in accordance with pre-designated dimensions: length×width×heights (L, H, W). Relevant dimensions for the various model studies are described further below.

The ensuing experiments illustrate the impact of creating spaces within the tablet structure, in particular the impact of 1) thickness of the block, 2) the space between blocks, 3) the number of bridges between the blocks and show its impact of breaking and dissolution time.

Example 6—Preparation of Filaments

Filaments for use in 3D FFF printing were produced in a similar manner to that described above in Example 1. Theophylline was used as a model drug and HPC was used a model polymer.

Approximately 12 g of the formulation comprising drug, polymer and other ingredients, was accurately weighed and then mixed in a mortar. The blend was gradually loaded into the extruder's heated barrel with rotating screws. The rotation speed has been set for 80 rpm. The composition was homogenized for around 5 minutes, allowing the components to uniformly melt and disperse. Operating parameters for fabricating the filaments by HME and for fused deposition modelling 3D printing were attained by Pietrzak et al. Temperature of the hot melt extrusion steps has been modified in order to optimize and simplify the process. Persistent temperature favoured uniformity of filaments (within and in between batches). Applied parameters are detailed in Table 5.

TABLE 5

Processing parameters of hot melt extrusion and FDM 3D printing.

| Hot melt extrusion | | | FDM 3D printing | | |
|---|---|---|---|---|---|
| Loading-mixing temperature (° C.) | Extruding temperature (° C.) | Nozzle diameter (mm) | Building plate temperature (° C.) | Extruding temperature (° C.) | Nozzle diameter (mm) |
| 120 | 120 | 1.7 | 160 | 60 | 0.4 |

After homogenization, the composition has been forced through a cylindrical shape die nozzle. The extruding force comes from the twin-screw rotations, enabling the material to flow out of the barrel. After leaving the heated barrel, the molten material solidifies in room temperature, forming a circular cross-section filament. Following these steps, two batches were produced from the prepared amount of compounds.

The filament thickness is determined by choosing the nozzle's diameter. In order to be able to apply the HPC-based filament for an FDM 3D printer, its thickness should not exceed over 1.75±0.05 mm.

Example 7—FFF (or FDM) 3D Printing of Tablets

The tablets were printed in accordance with the aforesaid skeletal structures using the printing apparatuses and methods set forth above under Examples 1-4.

Prototypes of product designs were developed with computer-aided design (CAD) software, i.e. 3ds Max software version 2015 (Autodesk Inc.). The obtained files were converted into a printer-readable format and imported to the printer's software in an STL format (Makerbot Desktop version 3.9.1).

Example 8—Morphology Testing

Digital photographs of the 3D printed tablets were acquired, using a Canon™ EOS 100D digital camera with EF-S 18-55 mm lens. Scanning electron microscopy was performed to obtain images of the tablets external surface. In order to prepare the printed tablets for imaging, gold coating was carried out. The samples were placed directly on adhesive carbon tabs, which had been applied on aluminum stubs. The stubs with samples were inserted into a JFC-1200 Fine Coater (Joel, Tokyo, Japan) and coated with gold for 2 minutes under vacuum. Afterwards, the samples surface was scanned using a Quanta-200 SEM microscope under vacuum and high voltage (20 kv).

Example 9—Dissolution Testing Protocols

The rate of drug release from the 3D printed tablets has been assessed using a dissolution test paddle apparatus (Erweka GmbH, Germany) in accordance with the United States Pharmacopeia requirements. The dissolution study for each tested tablet was conducted in 900 ml of 0.1 M hydrochloric acid (pH 1.2) at 37±0.5° C. and with paddle speed of 50 rpm. These conditions are to imitate the ones prevailing in human stomach. Every 5 minutes for 2 hours a UV/VIS spectrophotometer (PG Instruments Limited, UK) automatically measured absorbance of filtered portions of the tested solution at wavelength of 272 nm. The content of theophylline in each tablet exceeded 30 mg, therefore spectrophotometer cells chosen for this experiment had a 1 mm path length. Data was collected using IDIS software (Automated Lab, 2012) and the amount of released drug was calculated afterwards in Microsoft Office Excel. According to USP requirements, an immediate release tablet is considered as rapidly dissolving when at least 85% of the drug is released within 30 minutes.

Results and Discussion

Figure 16:
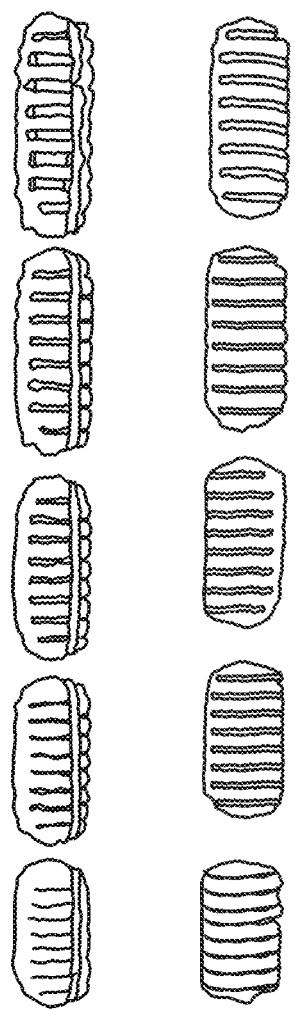
FIG. 16 shows a range of 1.0 mm (top) and 1.5 mm (bottom) block tablets with increasing spaces (0.2, 0.4, 0.6, 0.8, 1.0 and 1.2 mm) from left to right.

FIG. 16 shows a range of 1.0 mm (top) and 1.5 mm (bottom) block tablets with increasing spaces (0.2, 0.4, 0.6, 0.8, 1.0 and 1.2 mm) from left to right.

It was possible to print tablets with both 1.0 and 1.5 mm block using FDM 3D printing with increasing spacing (FIG. 16).

Figure 17:
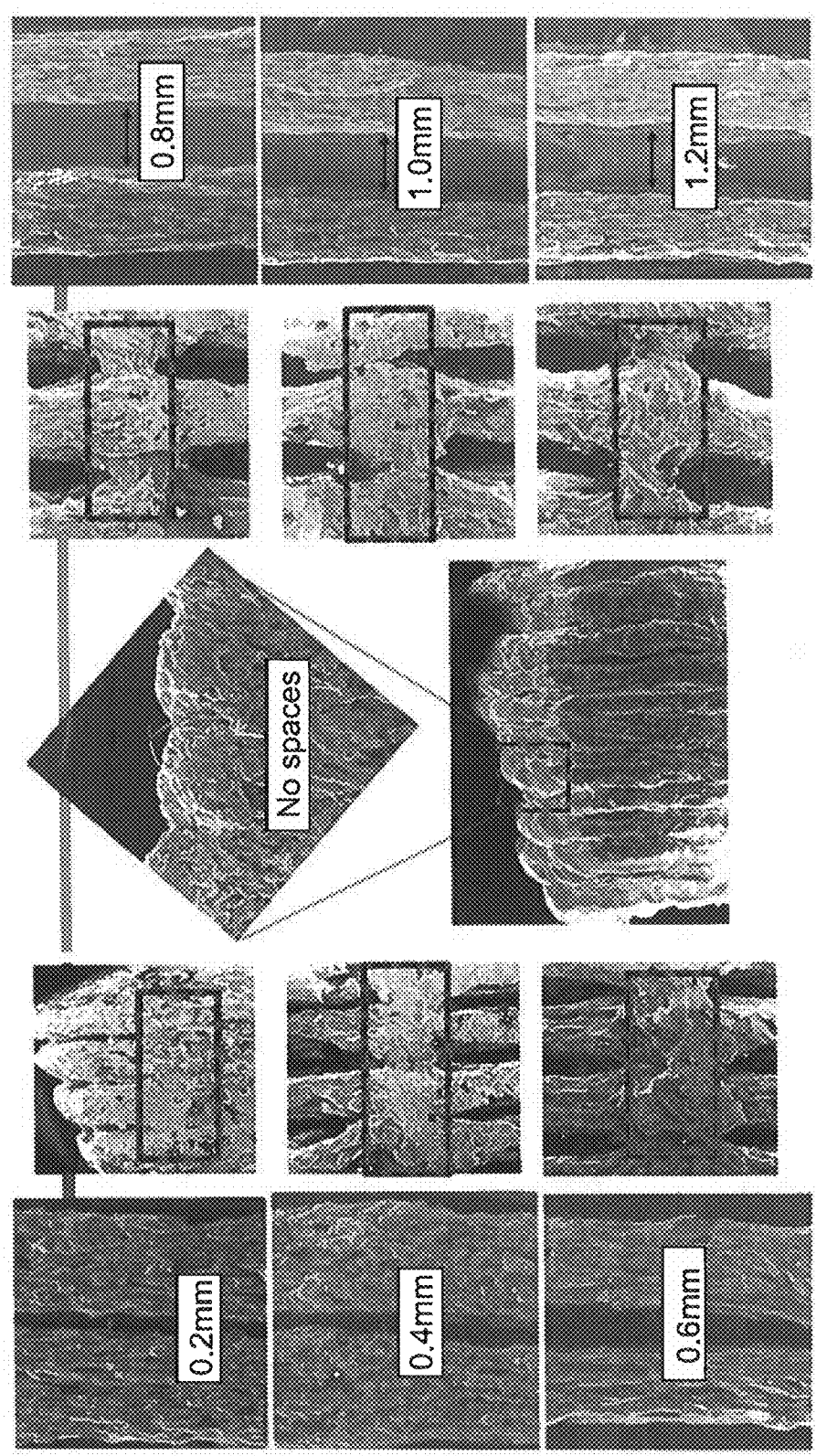
FIG. 17 shows SEM images of the weak joints between 1 mm block tablets with intervening spacings set at 0.2, 0.4, 0.6, 0.8, 1.0 and 1.2 mm.

FIG. 17 shows SEM images of the weak joints between 1 mm block tablets with intervening spacings set at 0.2, 0.4, 0.6, 0.8, 1.0 and 1.2 mm.

These SEM images indicated that the spaces between these blocks remained in the desired range.

The tablet design resulted in increased surface to volume and surface to mass ratios (Tables 6 and 7). However, such an increase is unlikely, by itself, to dramatically increase the dissolution rate.

FIG. 18 shows theophylline release profiles for a) 1.0 mm blocks and b) 1.5 mm blocks over with varying interblock spacings.

FIG. 18 indicated that the introduction of spaces between the blocks led to a significant increase in the dissolution rate for both 1.0 and 1.5 mm block series, with the 1.0 mm block series meeting the USP criteria for immediate release dissolution.

Figure 19:
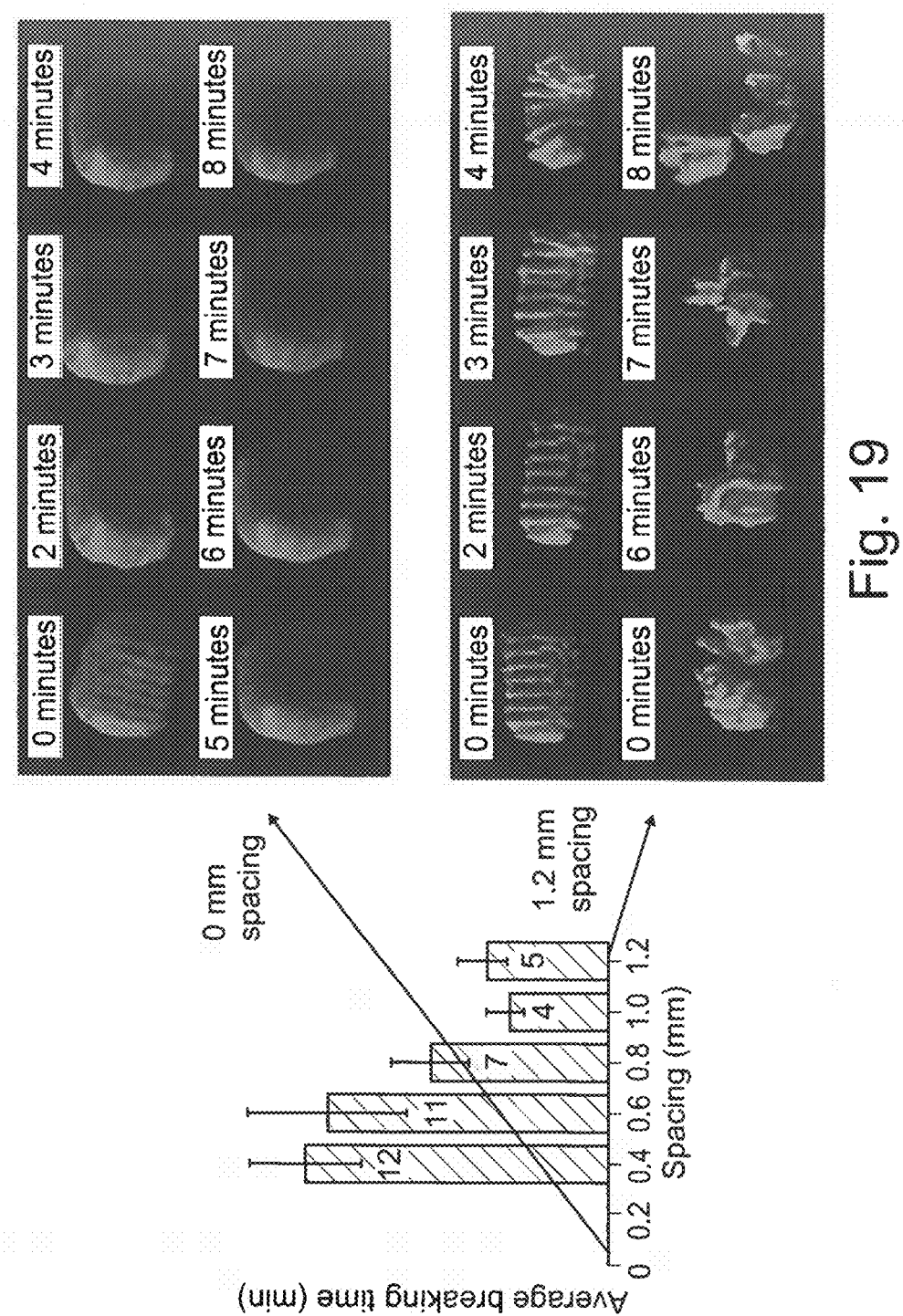
FIG. 19 shows a bar chart reporting the average breaking/disintegration times (in minutes) of 1 mm block-based tablets over a range of spacings (0 to 1.2 mm); green-laser-light images (top set) obtained during dissolution testing of a block tablet with 0 spacings (i.e. a complete block); and green-laser-light images (bottom set) obtained during dissolution testing of a tablet made of 1.0 mm block with and 1 mm spaces.

Though acceleration of drug release may be marginally increased by changing the mass/volume ratios, more importantly the skeletal weak-point containing designs allows the break-up of the tablet into smaller units as revealed by imaging the dissolution test (FIG. 19).

FIG. 19 shows (a) a bar chart reporting the average breaking/disintegration times (in minutes) of 1 mm block-based tablets over a range of spacings (0 to 1.2 mm); (b) green-laser-light images (top set) obtained during dissolution testing of a block tablet with 0 spacings (i.e. a complete block); and (c) green-laser-light images (bottom set) obtained during dissolution testing of a tablet made of 1.0 mm block with and 1 mm spaces.

Whilst the block and 2 mm spaces did not break, tablets with weak joint designs broke after 5-12 min of the onset of the dissolution test. These results suggest that a minimum spacing distance of ≥0.4 is needed to accelerate drug release from this system.

Figure 20:
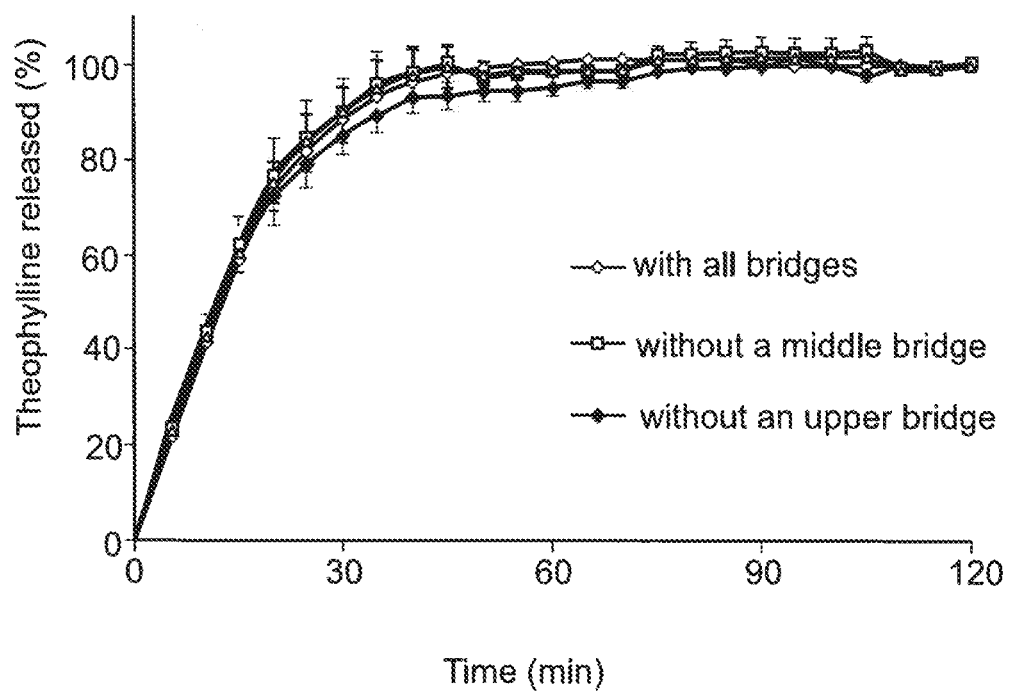
FIG. 20 shows theophylline release profiles over time for tablets with bridge modifications in 1.2 mm spaced 1.0 mm blocks.

In order to optimize the number of bridges between the blocks, the design was adjusted by removing one or more bridges. The lower bridge was potentially helpful for the integrity of the design and were kept in all of the tested examples. FIG. 20 indicated that reducing the number of bridges did not contribute to the improvement of the dissolution rate.

FIG. 20 shows theophylline release profiles over time for tablets with bridge modifications in 1.2 mm spaced 1.0 mm blocks.

TABLE 6

Characteristics of tablets obtained from 3ds Max software and average mass of tablets.

| Block thickness (mm) | Spaces (mm) | Tablet dimensions (mm) | | | Volume ($mm^3$) | Surface area ($mm^2$) | Average mass ± SD (mg) |
|---|---|---|---|---|---|---|---|
| | | X | Y | Z | | | |
| 1.5 | 0.0 | 13.50 | 6.55 | 7.13 | 158.93 | 853.81 | 583.15 ± 23.92 |
| 1.5 | 0.2 | 15.03 | 6.55 | 7.13 | 467.39 | 917.54 | 532.08 ± 53.62 |
| 1.5 | 0.4 | 16.64 | 6.55 | 7.13 | 470.14 | 929.52 | 529.20 ± 52.21 |
| 1.5 | 0.6 | 18.20 | 6.55 | 7.13 | 472.74 | 942.10 | 556.63 ± 21.20 |
| 1.5 | 0.8 | 19.80 | 6.55 | 7.13 | 475.38 | 956.15 | 531.94 ± 33.66 |
| 1.5 | 1.0 | 21.42 | 6.55 | 7.13 | 478.09 | 971.35 | 541.33 ± 40.80 |
| 1.5 | 1.2 | 23.06 | 6.55 | 7.13 | 480.67 | 986.67 | 534.25 ± 48.98 |
| 1.0 | 0.0 | 9.93 | 6.55 | 7.13 | 23.47 | 691.23 | 323.18 ± 24.26 |
| 1.0 | 0.2 | 11.52 | 6.55 | 7.13 | 328.96 | 839.98 | 320.56 ± 26.21 |
| 1.0 | 0.4 | 13.16 | 6.55 | 7.13 | 331.75 | 852.34 | 316.77 ± 21.53 |
| 1.0 | 0.6 | 14.71 | 6.55 | 7.13 | 334.37 | 864.31 | 326.86 ± 12.02 |
| 1.0 | 0.8 | 16.50 | 6.55 | 7.13 | 337.49 | 879.41 | 325.10 ± 12.67 |
| 1.0 | 1.0 | 18.01 | 6.55 | 7.13 | 339.90 | 893.50 | 337.29 ± 16.18 |
| 1.0 | 1.2 | 19.48 | 6.55 | 7.13 | 342.30 | 907.37 | 341.89 ± 19.84 |

TABLE 7

(Surface area:volume) and (surface area:average mass) ratios

| Block thickness (mm) | Spaces (mm) | (Surface area:volume) ratio | (Surface area:average mass) ratio |
|---|---|---|---|
| 1.5 | 0.0 | 5.37 | 1.46 |
| 1.5 | 0.2 | 1.96 | 1.72 |
| 1.5 | 0.4 | 1.98 | 1.76 |
| 1.5 | 0.6 | 1.99 | 1.69 |
| 1.5 | 0.8 | 2.01 | 1.80 |
| 1.5 | 1.0 | 2.03 | 1.79 |
| 1.5 | 1.2 | 2.05 | 1.85 |
| 1.0 | 0.0 | 29.45 | 2.14 |
| 1.0 | 0.2 | 2.55 | 2.62 |
| 1.0 | 0.4 | 2.57 | 2.69 |
| 1.0 | 0.6 | 2.58 | 2.64 |
| 1.0 | 0.8 | 2.61 | 2.71 |
| 1.0 | 1.0 | 2.63 | 2.65 |
| 1.0 | 1.2 | 2.65 | 2.65 |

Conclusion

It was possible to utilize an FDM 3D printer to achieve accelerated drug release from tablets, especially cellulosic-based tablets. Although it was feasible to incorporate disintegrants to tablets formulation, this approach generally did not significantly enhance drug release from FDM printed tablets. The "Gaplet" tablets (tablets divided into blocks with determined spaces in between) however performed extremely well in disintegration and dissolution tests. The "Gaplet" tablets have points susceptible to breaking, which allows the crafting of immediate drug release from the cellulose matrix. Increasing spacings between blocks slightly increases the tablets (surface area/mass) ratio, when compared to tablets without spacing, but the crucial reason for accelerated release profiles are the weak points, which cause the tablet to break in dissolution medium.

Further Embodiments

The present invention may be defined according to any one or more of the following numbered paragraphs:

1. A solid dosage form of a pharmaceutical, nutraceutical, or food supplement composition, for oral administration, the solid dosage form comprising one or more channels, preferably a plurality of channels, extending through the body (i.e. bulk) and/or a surface thereof.
2. The solid dosage form as defined in paragraph 1, wherein the solid dosage form is a 3D-printed solid dosage form, suitably a fused filament fabrication (FFF)-3D-printed solid dosage form.
3. The solid dosage form as defined in paragraph 2, wherein the presence of the one or more channels promotes faster disintegration and/or dissolution of the solid dosage form in comparison to an equivalent solid dosage form without said one or more channels.

4. The solid dosage form as defined in any of paragraphs 2 to 3, wherein the solid dosage form is an immediate release solid dosage form.
5. The solid dosage form as defined in paragraph 4, wherein the immediate release solid dosage form is an immediate release tablet.
6. The solid dosage form as defined in any of paragraphs 2 to 5, wherein the one or more channels comprise void space.
7. The solid dosage form as defined in any of paragraphs 2 to 6, wherein the channels ($V_{chan}$) constitute at least 5% of the overall channel-inclusive volume ($V_{tot}$) of the solid form and at most 40%.
8. The solid dosage form as defined in any of paragraphs 2 to 7, wherein the one or more channel(s) each have a channel cross-section, and the shortest dimension ($D_{min}$) of the channel cross-section(s) is greater than or equal to 0.4 mm and less than or equal to 4.0 mm.
9. The solid dosage form as defined in paragraph 8, wherein the shortest dimension ($D_{min}$) of the channel cross-section(s) is greater than or equal to 0.6 mm and less than or equal to 2.0 mm.
10. The solid dosage form as defined in paragraph 8 or 9, wherein the one or more channel(s) are independently tubular passages or grooves.
11. The solid dosage form as defined in paragraph 10, wherein the shape of the one or more channel cross-section(s) are independently selected from the group consisting of a circle, ellipse, hexagon, pentagon, square, rectangle, and triangle; and wherein the one or more channel(s) are optionally open-sided.
12. The solid dosage form as defined in paragraph 10 or 11, wherein at least one of the one or more channel(s) has at least one open-ended end or open-sided side.
13. The solid dosage form as defined in paragraph 12, wherein at least one of the one or more channel(s) comprises one or more cross-bridges along its length.
14. The solid dosage form as defined in paragraph 13, wherein any cross-bridges within a channel cross-bridge the shortest dimension of said channel.
15. The solid dosage form as defined in any of paragraphs 2 to 13, wherein the solid dosage form comprises a plurality of substantially parallel channels.
16. The solid dosage form as defined in any of paragraphs 2 to 15, wherein the solid dosage form comprises a plurality of double-open-ended tubular square or rectangular cross-sectioned channels extending through the entire body of the solid dosage form, wherein the shortest dimension of the cross-section of said channel(s) is at least 0.4 mm.
17. The solid dosage form as defined in any of paragraphs 2 to 16, wherein the solid dosage form comprises a plurality of tubular channels extending through the shortest dimension of the entire body of the solid dosage form.
18. The solid dosage form as defined in any of paragraphs 2 to 17, wherein the solid dosage form comprises a plurality of grooved channels extending through at least part of the body of the solid dosage form.
19. The solid dosage form as defined in any of paragraphs 2 to 18, wherein the dosage form comprises a plurality of interconnected dosage sub-units, wherein adjacent sub-units are interconnected by one or more intervening frangible cross-links (e.g. "weak points"), suitably which break upon contact with a dissolution medium to release a plurality of separated dosage sub-units.
20. The solid dosage form as defined in any of paragraphs 2 to 19, wherein the solid dosage form comprises within its body greater than or equal to 10 wt % carrier material, wherein the carrier material has a molecular weight of at least 10,000.
21. The solid dosage form as defined in paragraph 20, wherein the carrier material is a compound that is sparingly soluble, slightly soluble, very slightly soluble, practically insoluble, or insoluble according to the standard USP definitions.
22. The solid dosage form as defined in any of paragraphs 18 to 21, wherein the solid dosage form has a glass transition temperature between 30 and 200° C.
23. The solid dosage form as defined in any of paragraphs 18 to 22, wherein the carrier material is a polymer or copolymer.
24. The solid dosage form as defined in paragraph 23, wherein the carrier material is a polymer or mixture of polymers selected from the group consisting of an (optionally alkyl-) acrylate, methacrylate or ethacrylate polymer or copolymer, optionally comprising amine-containing monomeric units, a polyvinylpyrrolidone or polyvinylpyrrolidone-derived polymer or co-polymer, and a polyalkyleneglycol or polyalkyleneglycol-derived polymer or copolymer.
25. The solid dosage form as defined in any of paragraphs 2 to 24, wherein the solid dosage form has a "solid-volume-based surface area density" ($d_{Asol}$) greater than or equal to 1.0 mm$^{-1}$, wherein the "solid-volume-based surface area density" ($d_{Asol}$) is defined by the equation:

$$d_{Asol} = \frac{A_{tot}}{V_{sol}}$$

wherein $A_{tot}$ is the overall surface area of the solid dosage form, including any internal and external surfaces thereof; and
wherein $V_{sol}$ is solid volume only, exclusive of the volume of any channel(s), and is greater than or equal to 300 mm$^3$.
26. A solid dosage form printing apparatus for printing a solid dosage form as defined in any preceding paragraph, the apparatus comprising:
a 3D printer;
a build platform upon which the solid form is printable;
a body printing composition or filament comprising a carrier material (suitably as defined in any of paragraphs 23 to 25);
optionally a channel printing composition or filament comprising a channel material (suitably as defined herein); and
a computer for controlling the 3D printer;
wherein the 3D printer is operable via the computer running pursuant to specialist solid dosage form printing software, and optionally also to one or more databases, and configured to operate the 3D printer to print the solid dosage form upon the build platform via a process involving the printing and/or extrusion of the printing composition(s) or filament(s) to produce a solid dosage form comprising one or more channel(s), wherein the channel(s) comprise void space and/or a channel material.
27. The solid dosage form printing apparatus as defined in paragraph 26, wherein the 3D printer is a fused filament fabrication 3-dimensional printer (an FFF 3D printer).

28. A computer-implemented method of preparing (or printing) a solid dosage form as defined in any of paragraphs 1 to 25, the method comprising:
 a) providing a solid form printing apparatus, the apparatus comprising:
  a 3D printer (suitably an FFF 3D printer);
  a build platform upon which the solid form is printable;
  a body printing (ink, or filament) composition comprising a carrier material optionally mixed with one or more additional ingredients (e.g. a pharmaceutical active);
  optionally a channel printing (ink, or filament) composition comprising a channel material optionally mixed with one or more addition ingredients (e.g. a pharmaceutical active); and
  a computer for controlling the 3D printer running pursuant to specialist solid dosage form printing software, and optionally also to one or more databases;
 b) operating the 3D printer via the computer to print the solid dosage form upon the build platform via a computer-implemented process comprising:
  i) printing (and/or extruding) the body printing composition to form the or part of a body of the solid form; and
  either
   I. leaving channels of void space(s) within the body or surface of the solid form; or
   II. printing (and/or extruding) the channel printing composition to form channels of channel material within the body or surface of the solid form;
 c) optionally performing one or more further processing steps (with or without the 3D printer; e.g. coating or otherwise modifying the surface, shape, or properties of the solid form).

29. A solid dosage form obtainable by the computer-implemented method of paragraph 28.

30. A computer program, comprising solid dosage form printing software code for performing the computer-implemented method of paragraph 28 when the computer program is run on a computer.

The invention claimed is:

1. A solid dosage form comprising a plurality of channels extending through the body and/or a surface thereof;
 wherein each of the plurality of channels comprises either or both:
  i) empty space; and/or
  ii) a channel material which disintegrates and/or dissolves at a faster rate than other parts or the solid dosage form;
 wherein the solid dosage form comprises an active ingredient;
 wherein the overall volume ($V_{tot}$) of the solid dosage form, inclusive of the volume of any channels, is 50-5000 mm$^3$;
 wherein the solid dosage form is characterised by a percentage channel volume of 2-30%, where the percentage channel volume is expressable as:

$$\frac{V_{chan}}{V_{tot}} \times 100$$

wherein $V_{chan}$ is the total volume of the channels and $V_{tot}$ is the overall volume of the solid dosage form.

2. The solid dosage form as claimed in claim 1, wherein the channels are continuous or extended regions within the body of the solid dosage form.

3. The solid dosage form as claimed in claim 2, wherein each channel is independently characterised by a particular channel cross-section which extends along at least part of the length of the channel, and the shortest dimension ($D_{min}$) of the cross-section is greater than or equal to 0.2 mm.

4. The solid dosage form as claimed in claim 3, wherein at least one of the channels has at least one open-ended end or open-sided side such that the at least one of the channels is linked to the exterior of the solid dosage form.

5. The solid dosage form as claimed in claim 4, wherein the channels are grooves, trenches, or slices within the solid dosage form, optionally with cross-links or bridges between opposite sides of the channels.

6. The solid dosage form as claimed in claim 5, wherein the channels are grooves whose depth constitutes greater than or equal to 70% of the total depth of the solid form in the particular direction of the groove.

7. The solid dosage form as claimed in claim 5, wherein the solid dosage form comprises a plurality of interconnected dosage sub-units, wherein adjacent sub-units are interconnected by one or more intervening frangible cross-links or bridges.

8. The solid dosage form as claimed in claim 7, wherein the dosage sub-units are spaced by a gap of at least 0.4 mm.

9. The solid dosage form as claimed in claim 7, wherein the cross-links and solid dosage form breaks into a plurality of separated dosage sub-units upon contact with a disintegration/dissolution medium.

10. The solid dosage form as claimed in claim 1, wherein the solid dosage form comprises a plurality of substantially parallel channels.

11. The solid dosage form as claimed in claim 10, wherein the solid dosage form comprises within its body greater than or equal to 10 wt % carrier material, wherein the carrier material has a molecular weight of at least 10,000.

12. The solid dosage form as claimed in claim 11, wherein the carrier material is a polymer or copolymer.

13. The solid dosage form as claimed in claim 1, wherein the solid dosage form is a 3D-printed solid dosage form.

14. The solid dosage form as claimed in claim 1, wherein the solid dosage form is an immediate release solid dosage form of a pharmaceutical, nutraceutical, or food supplement composition, for oral administration, the solid dosage form comprising a plurality of interconnected dosage sub-units, wherein adjacent sub-units are interconnected by one or more intervening frangible cross-links or bridges traversing channels of void space extending through the body of the solid dosage form, such that the dosage sub-units are spaced by a gap of 0.4-2 mm;
 wherein the channels are slices of void space linked to the exterior of the solid dosage form and individual sub-units are individual blocks, sheets, or discs;
 wherein the cross-links and solid dosage form breaks into a plurality of separated dosage sub-units upon contact with a disintegration/dissolution medium.

15. The solid dosage form as claimed in claim 1, wherein the solid dosage form is an immediate release solid dosage form of a pharmaceutical, nutraceutical, or food supplement composition, for oral administration, the solid dosage form comprising a plurality of channels extending through the body thereof; wherein the channels are continuous or extended regions within the body of the solid dosage form characterised by a channel material which is dissimilar to and disintegrates and/or dissolves at a faster rate than surrounding material within the solid dosage form; wherein each channel has a channel cross-section whose shortest dimension ($D_{min}$) is greater than or equal to 0.2 mm and whose longest dimension ($D_{min}$) is less than or equal to 2.0 mm; wherein at least one of the channels is open at the surface of the solid dosage form.

16. A solid dosage form printing apparatus for printing a solid dosage form, the apparatus comprising:
- a 3D printer;
- a build platform upon which the solid form is printable;
- a body printing composition or filament comprising a carrier material; and
- a computer for controlling the 3D printer;

wherein the 3D printer is operable via the computer running pursuant to specialist solid dosage form printing software, and optionally also to one or more databases, and configured to operate the 3D printer to print the solid dosage form upon the build platform via a process involving the printing and/or extrusion of the body printing composition(s) or filament(s) to produce a solid dosage form comprising a plurality of channels, wherein the channels comprise void space and/or a channel material.

17. A computer-implemented method of preparing (or printing) a solid dosage form as claimed in claim 1, the method comprising:
a) providing a solid form printing apparatus, the apparatus comprising:
- a 3D printer;
- a build platform upon which the solid form is printable;
- a body printing composition comprising a carrier material optionally mixed with one or more additional ingredients; and
- a computer for controlling the 3D printer running pursuant to specialist solid dosage form printing software, and optionally also to one or more databases;
b) operating the 3D printer via the computer to print the solid dosage form upon the build platform via a computer-implemented process comprising:
i) printing the body printing composition to form the or part of a body of the solid dosage form; and
ii) leaving channels of void space(s) within the body or surface of the solid form and optionally thereafter printing a channel material within said void space(s); and
c) optionally performing one or more further processing steps (with or without the 3D printer.

18. A computer program, comprising solid dosage form printing software code for performing the computer-implemented method of claim 17 when the computer program is run on a computer.

19. The solid dosage form as claimed in claim 3, wherein each channel is independently characterised by a particular channel cross-section which extends and is preserved in terms of shape and/or dimensions along at least part of the length of the channel.

20. The solid dosage form as claimed in claim 3, wherein the shortest dimension ($D_{min}$) of the cross-section is greater than or equal to 0.4 mm.

21. The solid dosage form as claimed in claim 4, wherein at least one of the channels has at least one open-ended end or open-sided side such that the at least one of the channels is linked to the exterior of the solid dosage form with channel openings at the surface of the solid dosage form.

22. The solid dosage form as claimed in claim 9, wherein the disintegration/dissolution medium is gastric fluid.

23. The solid dosage form as claimed in claim 13, wherein the 3D-printed solid dosage form is a fused filament fabrication (FFF)-3D-printed solid dosage form.

24. The solid dosage form as claimed in claim 1, wherein the solid dosage form has a solid-volume-based surface area density ($d_{Asol}$) between 0.8 mm$^{-1}$ and 3 mm$^{-1}$; wherein the solid-volume-based surface area density ($d_{Asol}$) is expressible as:

$$d_{Asol} = \frac{A_{tot}}{V_{sol}}$$

where $A_{tot}$, is the overall surface area, and $V_{sol}$ is solid volume only exclusive of the volume of any channels.

25. The solid dosage form as claimed in claim 24, wherein the solid dosage form has a solid-volume-based surface area density ($d_{Asol}$) between 1.2 mm$^{-1}$ and 2 mm$^{-1}$.

* * * * *